(12) United States Patent
Sawant et al.

(10) Patent No.: US 8,410,323 B2
(45) Date of Patent: Apr. 2, 2013

(54) PROCESS FOR DOWNSTREAM RECOVERY OF NITROALKANE USING DIVIDING WALL COLUMN

(75) Inventors: Mahesh Sawant, Pune (IN); Daniel M. Trauth, Crystal Lake, IL (US); John G. Pendergast, Jr., Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 236 days.

(21) Appl. No.: 12/879,814

(22) Filed: Sep. 10, 2010

(65) Prior Publication Data
US 2011/0092749 A1    Apr. 21, 2011

(30) Foreign Application Priority Data
Oct. 20, 2009    (IN) .................. 2540/CHE/2009

(51) Int. Cl.
*C07C 205/00* (2006.01)
(52) U.S. Cl. ........................................ 568/948
(58) Field of Classification Search ........... 568/948
See application file for complete search history.

(56) References Cited

U.S. PATENT DOCUMENTS

| | | |
|---|---|---|
| 1,967,667 A | 7/1934 | Hass et al. |
| 2,343,534 A | 3/1944 | Cavanaugh et al. |
| 2,418,241 A | 4/1947 | Stengel et al. |
| 2,455,425 A | 12/1948 | Levy et al. |
| 2,465,959 A | 3/1949 | Tindall |
| 2,489,320 A | 11/1949 | Nygaard et al. |
| 2,491,919 A | 12/1949 | Egly |
| 2,511,454 A | 6/1950 | Bishop et al. |
| 2,512,587 A | 6/1950 | Stengel |
| 2,575,855 A | 11/1951 | Stengel et al. |
| 2,654,658 A | 10/1953 | Marshall |
| 2,654,788 A | 10/1953 | Marshall |
| 2,789,136 A | 4/1957 | O'hara |
| 2,844,634 A | 7/1958 | McKinnis |
| 3,035,100 A | 5/1962 | Kirby et al. |
| 3,133,124 A | 5/1964 | Bonfield |
| 3,173,961 A | 3/1965 | Drimus et al. |
| 3,657,364 A | 4/1972 | Crawford et al. |
| 3,869,253 A | 3/1975 | L'honore et al. |
| 3,917,705 A | 11/1975 | Swanson et al. |
| 4,313,009 A | 1/1982 | L'honore et al. |
| 4,329,523 A | 5/1982 | James et al. |
| 4,394,220 A | 7/1983 | Egly et al. |
| 4,458,094 A | 7/1984 | Sherwin |
| 4,476,336 A | 10/1984 | Sherwin |

(Continued)

FOREIGN PATENT DOCUMENTS

| | | |
|---|---|---|
| EP | 0151074 A2 | 8/1985 |
| EP | 0171052 A2 | 2/1986 |

(Continued)

OTHER PUBLICATIONS

PCT International Search Report, PCT International Application No. PCT/US2010/048487, mailed Mar. 2, 2011.

(Continued)

*Primary Examiner* — Jafar Parsa
(74) *Attorney, Agent, or Firm* — McDonnell Boehnen Hulbert & Berghoff LLP

(57) ABSTRACT

Disclosed are a process and apparatus for synthesizing nitroalkanes by reaction of a hydrocarbon feedstock with aqueous nitric acid. Energy and capital costs may be reduced by using a dividing wall column.

16 Claims, 17 Drawing Sheets

U.S. PATENT DOCUMENTS

| | | | |
|---|---|---|---|
| 4,518,811 | A | 5/1985 | Lhonore et al. |
| 4,626,607 | A | 12/1986 | Jacquinot et al. |
| 2011/0028731 | A1 | 2/2011 | Trauth et al. |
| 2011/0028732 | A1 | 2/2011 | Trauth et al. |
| 2011/0092737 | A1 | 4/2011 | Trauth |
| 2011/0092748 | A1 | 4/2011 | Sawant et al. |
| 2011/0092750 | A1 | 4/2011 | Trauth et al. |
| 2011/0160496 | A1 | 6/2011 | Sawant et al. |

FOREIGN PATENT DOCUMENTS

| | | |
|---|---|---|
| GB | 916954 | 1/1963 |
| WO | WO2009129099 | 10/2009 |
| WO | WO2011049681 | 4/2011 |
| WO | WO2011049682 | 4/2011 |
| WO | WO2011049683 | 4/2011 |
| WO | WO2011078931 | 6/2011 |

OTHER PUBLICATIONS

Olujic Z. et al., "Equipment improvement trend in distillation", Chemical Engineering and Processing, vol. 48, Mar. 26, 2009, pp. 1089-1104.
PCT International Search Report and Written Opinion, PCT International Application No. PCT/US2010/048487, mailed Feb. 28, 2011.
PCT Written Opinion of the International Preliminary Examining Authority, PCT International Application No. PCT/US2010/048482, mailed Oct. 18, 2011.
PCT International Preliminary Report on Patentability, PCT International Application No. PCT/US2010/048482, mailed Jan. 24, 2012.
PCT International Search Report and PCT Written Opinion, PCT International Application No. PCT/US2010/048482, mailed Nov. 17, 2010.
Albright, Lyle F., Nitration of Paraffins, Chemical Engineering, Jun. 6, 1966, pp. 149-156.
PCT Written Opinion of the International Preliminary Examining Authority, PCT International Application No. PCT/US2010/048487, mailed Oct. 18, 2011.
PCT International Preliminary Report on Patentability, PCT International Application No. PCT/US2010/048487, mailed Feb. 20, 2012.
PCT International Search Report, PCT International Application No. PCT/US2010/048487, mailed Feb. 28, 2011.
PCT Written Opinion of the International Preliminary Examining Authority, PCT International Application No. PCT/US2010/057628, mailed Feb. 14, 2012.
PCT International Preliminary Report on Patentability, PCT International Application No. PCT/US201048480, mailed May 3, 2012.
PCT International Search Report, PCT International Application No. PCT/US2010048480, mailed Mar. 2, 2011.
PCT International Preliminary Report on Patentability, PCT International Application No. PCT/US2010/057628, mailed Jul. 6, 2012.
PCT Written Opinion of the International Preliminary Examining Authority, PCT International Application No. PCT/US2010/057628, mailed Apr. 4, 2012.
PCT International Search Report and Written Opinion, PCT International Application No. PCT/US2010/057628, mailed Mar. 31, 2011.
Reply to Written Opinion, PCT International Application No. PCT/US2010/048482, filed Aug. 16, 2011.
Reply to Written Opinion, PCT International Application No. PCT/US2010/048487, filed Aug. 16, 2011.
Reply to Written Opinion, PCT International Application No. PCT/US2010/057628, filed Oct. 19, 2011.
Office Action, U.S. Appl. No. 12/879,799, mailed Aug. 30, 2012.
Office Action U.S. Appl. No. 12/879,824, mailed Sep. 21, 2012.

Impurity response to liquid split ratio at 881 BTU/lb

PROCESS FOR DOWNSTREAM RECOVERY OF NITROALKANE USING DIVIDING WALL COLUMN

CROSS-REFERENCE TO RELATED APPLICATIONS

This application claims priority to Indian Provisional Application No. 2540/CHE/2009, filed Oct. 20, 2009, which is hereby incorporated herein by reference in its entirety.

FIELD

The invention relates to a process for synthesizing nitroalkanes. More specifically, the invention relates to a process for intensified nitroalkane recovery in which a dividing wall column is used.

BACKGROUND

The nitration of hydrocarbons produces a variety of products, depending on the reaction conditions and the feedstock compositions. For example, vapor phase nitration of propane typically results in a mixture of four nitro-paraffin products: nitromethane, 1-nitropropane, 2-nitropropane, and nitroethane in essentially fixed relative concentrations. High pressure nitration of propane can selectively produce 2-nitropropane over other lower molecular weight nitroalkanes like 1-nitropropane, nitromethane, and nitroethane. The high pressure nitration of cyclohexane typically results in the formation of cyclohexanol, cyclohexanone, nitrocyclohexane, and oxidation products.

The byproducts from typical vapor phase and high pressure nitration of propane, can have similar boiling points, especially among the low molecular weight nitroalkanes (2-nitropropane, 1-nitropropane, nitromethane, and nitroethane), making separation difficult. A conventional post-reaction distillation sequence uses tall columns and high reflux ratios, which are expensive and consume a lot of energy. Other conventional separation methods use an additional mass-separating agent to recover the desired nitro-paraffin. A need exists, therefore, for more economical and energy efficient processes for recovering desired nitroalkane products.

BRIEF SUMMARY

In one aspect, a process is provided for synthesizing at least one nitroalkane. The process comprises: reacting in a reactor a hydrocarbon feedstock with aqueous nitric acid, such that a product stream is produced; separating the product stream into at least an oil phase and an aqueous phase; removing substantially all organic acids from the oil phase; thereafter, distilling the oil phase in a dividing wall column, to recover at least a top product, a middle product, and a bottom product; and recovering the at least one nitroalkane from the middle product.

In another aspect, a process for nitroalkane recovery is provided. The process comprises: separating a product stream from a nitroparaffin nitration process into at least an oil phase and an aqueous phase; distilling the oil phase in a dividing wall column, to recover at least a top product, a middle product, and a bottom product; recovering at least a first nitroalkane from the middle product; and recovering at least a second nitroalkane from the bottom product.

In yet another aspect, an apparatus for synthesizing at least one nitroalkane is provided. The apparatus comprises: a reactor for reacting a hydrocarbon feedstock with aqueous nitric acid to form a reaction product stream; a phase separation apparatus for separating the reaction product stream into at least an oil phase and an aqueous phase; and a dividing wall column for distilling the oil phase into at least a top product, a middle product, and a bottom product, wherein the middle product comprises at least a portion of the at least one nitroalkane.

DETAILED DESCRIPTION

In one aspect, a process for synthesizing at least one nitroalkane is provided. This process may beneficially use a dividing wall column instead of two distillation columns to recover at least one nitroalkane, therefore reducing the capital and energy costs associated with the synthesis of nitroalkanes.

Figure 1:
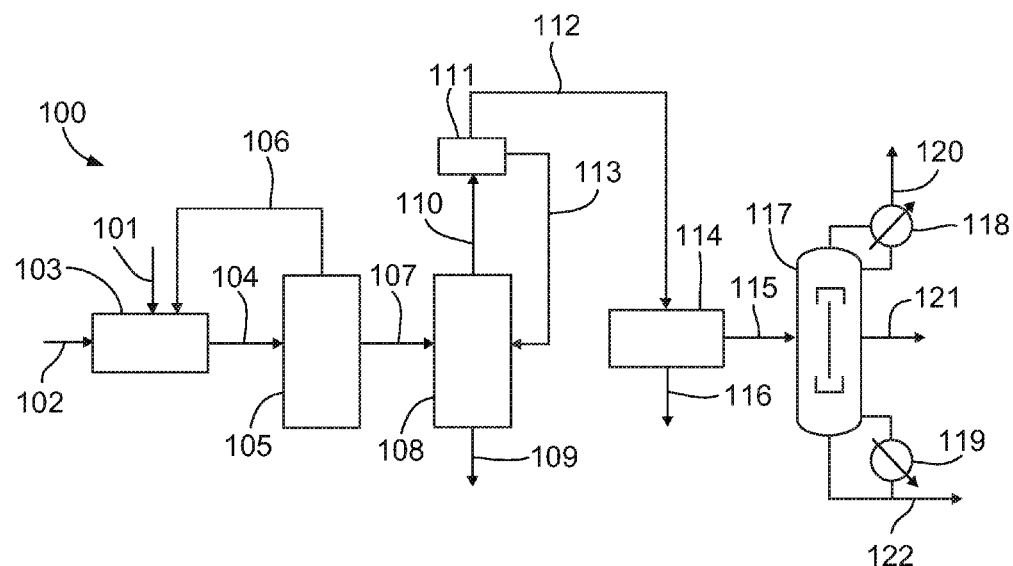
FIG. 1 is a schematic diagram of an apparatus for synthesizing at least one nitroalkane, in accordance with an illustrative embodiment.

FIG. 1 illustrates an apparatus 100 for synthesizing at least one nitroalkane. A hydrocarbon feedstock 101 and aqueous nitric acid 102 may be introduced into a reactor 103. The hydrocarbon feedstock 101 and the aqueous nitric acid 102 may react at a reactor pressure and a reaction temperature, such that a product stream 104 comprising nitrated compounds and byproducts may be formed.

The hydrocarbon feedstock 101 and the aqueous nitric acid 102 may be mixed, or partially mixed, prior to entry into the reactor 103 or, alternatively; they may be added individually, with mixing to occur within the reactor 103. Further, hydrocarbon feedstock 101 and the aqueous nitric acid 102, whether added together or individually, may be preheated prior to entry into the reactor 103.

In one example, the hydrocarbon feedstock 101 may consist essentially of propane and acetic acid. In other examples, the hydrocarbon feedstock 101 may include, without limitation, one or more of the following: alkanes and cycloalkanes (including alkyl substituted cycloalkanes), such as propane, isobutane, n-butane, isopentane, n-pentane, n-hexane, n-heptane, n-octane, 2,3-dimethylbutane, cyclohexane, cyclopentane, and methylcyclohexane; aryl alkanes such as ethylbenzene, toluene, xylenes, isopropyl benzene; 1-methylnaphthalene and 2-methylnaphthalene and 4-methylbiphenyl; fused cycloalkanes; alkyl substituted fused aryl compounds; fused cycloalkane-aryl compounds (including alkyl substituted derivatives), such as tetralin, decalin, and methylnaphthalene; and carboxylic acids, such as acetic acid, propanoic acid, butanoic acid, and hexanoic acid. The nitration of reactants that already have one or more nitro substituents is also contemplated provided that the reactant still has an available hydrogen.

The aqueous nitric acid may be delivered to the reactor 103 in the form of an aqueous solution that contains at least about 10 weight percent, preferably at least about 15 weight percent, more preferably at least about 20 weight percent, of the acid. Further, the solution may contain less than about 50 weight percent, preferably less than about 40 weight percent, and more preferably less than about 35 weight percent, of the acid. In further embodiments, the nitric acid solution may contain between about 15 and about 40 weight percent of the acid. In other embodiments, the nitric acid solution may contain between about 18 and about 35 weight of the acid.

The mole ratio of they hydrocarbon feedstock 101 to the aqueous nitric acid 102 may be at least about 0.3:1, more preferably at least about 0.5:1.

The reactor pressure may be at least about 500 psi (34 atm), preferably at least about 1000 psi (68 atm), and more preferably at least about 1200 psi (82 atm). Further, the pressure may be less than about 1600 psi (109 atm), preferably less than about 1500 psi (102 atm), and more preferably less than about 1400 psi (95 atm). In other embodiments, the pressure may between about 1000 psi (68 atm) and 1400 psi (95 atm). Various methods known in the art may be used for maintaining the pressure within the desired range including, for example, through the use of a back-pressure regulator.

The reaction temperature within the reactor may be controlled (for example with heat exchange fluid or using heat generated from the reaction) to greater than about 140 degrees Celsius and less than about 325 degrees Celsius. In other embodiments, the temperature may be greater than about 215 degrees Celsius and less than about 325 degrees Celsius. In some embodiments, the temperature may be greater than about 180 degrees, greater than about 200 degrees, greater than about 230 degrees, or greater than about 240 degrees. In further embodiments, the temperature may be less than about 290 degrees, less than about 280 degrees, less than about 270 degrees, or less than about 250 degrees. In other embodiments, the temperature may be between about 200 and 250 degrees Celsius. In yet further embodiments, the temperature may be between about 215 and 280 degrees Celsius, or between about 220 and 270 degrees Celsius.

Residence time of the reactants in the reactor 103 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 103 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

The reactor 103 may also be packed with a packing material to improve reactant mixing and heat transfer and/or to vary the reactor volume. Packing of the reactor may be preferred, for example, in a propane nitration system where it is desired to increase the concentration of 2,2-dinitropropane in the product stream. Suitable packing materials include, for example, glass beads, random packing, or structured packing, such as those typically employed in distillation devices. Other packing materials are known in the art and may be used.

The product stream 104 may then enter an absorber 105 for absorbing water-soluble and oil soluble components from the product stream 104 to form a hydrocarbon gas stream 106 and a gas-recovered mixture 107. The hydrocarbon gas stream 106 may contain unreacted hydrocarbons, carbon monoxide, carbon dioxide, nitric oxide, nitrous oxide, and nitrogen. The unreacted hydrocarbons in the hydrocarbon gas stream 106 may be recycled to the reactor 103. The remaining gases in the hydrocarbon gas stream 106 may be processed to recover nitric oxide as nitric acid. The further remaining gases in the hydrocarbon gas stream 106 may be sent through a burner and emitted. The gas-recovered mixture 107 may then enter a stripper 108 where an aqueous phase 109 may be stripped from the gas-recovered mixture 107 to form a second gas-recovered mixture 110. Next, the second gas-recovered mixture 110 may enter separator 111, where the second gas-recovered mixture 110 is separated into an oil phase 112 and a second aqueous phase 113. The second aqueous phase 113 may be recycled back to the phase separation apparatus 108. The aqueous phase 109 from the phase separation apparatus 108 may be disposed of or further recycled back to the reactor 103. The oil phase 112 may then enter a neutralization/waterwash apparatus 114 where substantially all the organic acids may be removed from the oil phase 112, resulting in at least a neutralized oil phase 115 and a waste stream 116. The neutralized oil phase 115 then may enter a dividing wall column 117, which may distill the neutralized oil phase 115.

The dividing wall column 117 may be operated at a vapor split ratio of between about 0.3:0.7 and 0.7:0.3, preferably between about 0.4:0.6 and 0.6:0.4, and more preferably about 0.5:0.5. The dividing wall column 117 may be operated at a liquid split ratio of between about 0.2:0.8 and 0.8:02, preferably between about 0.3:0.7 and 0.7:0.3, and more preferably between about 0.3:0.7 and 0.5:0.5. In other embodiments, the liquid split ratio may be between about 0.35:0.65 and 0.4:0.6, preferably about 0.37:0.63. In yet other embodiments, the liquid split ratio may be preferably about 0.35:0.65. In further embodiments, the liquid split ratio may be between about 0.45:0.65 and 0.5:0.5, preferably about 0.46:0.54.

The dividing wall column 117 may include a condenser 118 and a reboiler 119. The condenser 118 may be operated at a temperature between 20 and 80 degrees Celsius. The reboiler 119 may be operated at a temperature between 75 and 85 degrees Celsius.

The dividing wall column 117 may recover at least a top product 120, a middle product 121, and a bottom product 122. At least one nitroalkane may be recovered from the middle product 121. Examples of nitroalkanes that may be recovered include, among others, 2-nitropropane and nitrocyclohexane.

Figure 2:
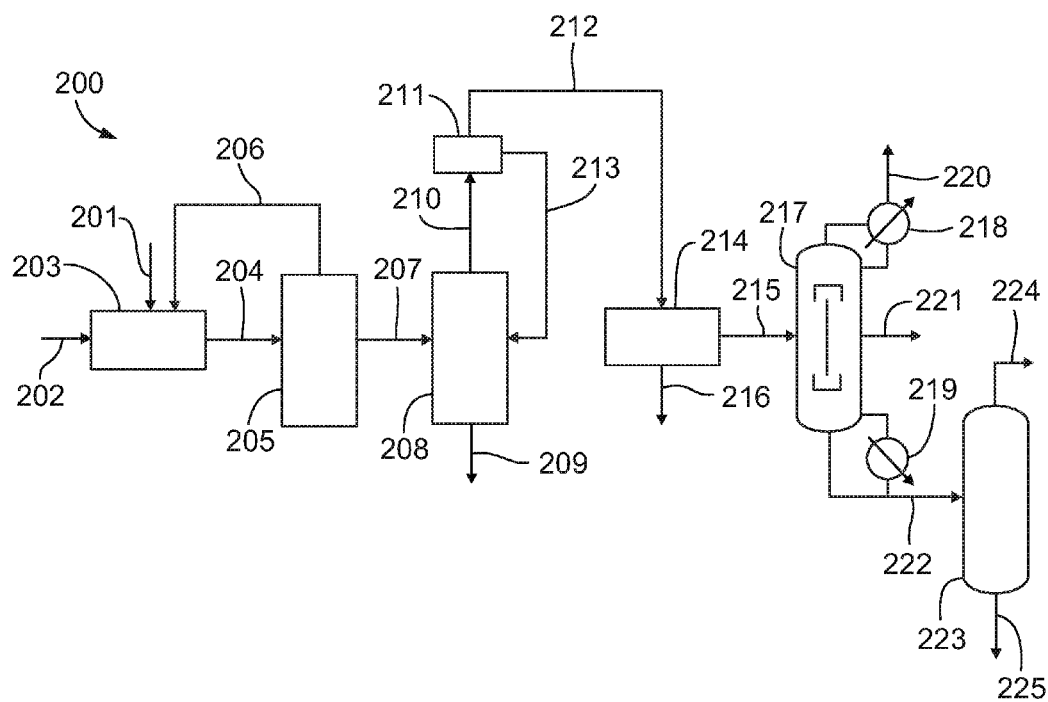
FIG. 2 is a schematic diagram of an apparatus for synthesizing at least a first nitroalkane and a second nitroalkane, in accordance with an illustrative embodiment.

FIG. 2 illustrates an apparatus 200 for synthesizing one or more nitroalkanes. A hydrocarbon feedstock 201 and aqueous nitric acid 202 may be introduced into a reactor 203. Reactor 203 may be similar to reactor 103 in FIG. 1. The hydrocarbon feedstock 201 and the aqueous nitric acid 202 may react at a reactor pressure and a reaction temperature, such that a product stream 204 comprising nitrated compounds and byproducts may be formed.

The hydrocarbon feedstock 201 and the aqueous nitric acid 202 may be mixed, or partially mixed, prior to entry into the reactor 203 or, alternatively; they may be added individually, with mixing to occur within the reactor 203. Further, hydrocarbon feedstock 201 and the aqueous nitric acid 202, whether added together or individually, may be preheated prior to entry into the reactor 203.

The hydrocarbon feedstock 201 may be similar to the hydrocarbon feedstock 101 in FIG. 1. The aqueous nitric acid 202 may have a similar composition as the aqueous nitric acid 102 in FIG. 1. The mole ratio of they hydrocarbon feedstock 201 to the aqueous nitric acid 202 may be at least about 0.3:1, more preferably at least about 0.5:1. The reactor pressure, reaction temperature, and residence time may be similar to that in FIG. 1.

The product stream 204 may then enter an absorber 205 for absorbing water-soluble and oil soluble components from the product stream 204 to form a hydrocarbon gas stream 206 and a gas-recovered mixture 207. The hydrocarbon gas stream 206 may contain unreacted hydrocarbons, carbon monoxide, carbon dioxide, nitric oxide, nitrous oxide, and nitrogen. The unreacted hydrocarbons in the hydrocarbon gas stream 206 may be recycled to the reactor 203. The remaining gases in the hydrocarbon gas stream 206 may be processed to recover nitric oxide as nitric acid. The further remaining gases in the hydrocarbon gas stream 206 may be sent through a burner and emitted. The gas-recovered mixture 207 may then enter a stripper 208 where an aqueous phase 209 may be stripped from the gas-recovered mixture 207 to form a second gas-recovered mixture 210. Next, the second gas-recovered mixture 210 may enter separator 211, where the second gas-recovered mixture 210 is separated into an oil phase 212 and a second aqueous phase 213. The second aqueous phase 213 may be recycled back to the phase separation apparatus 208. The aqueous phase 209 from the phase separation apparatus 208 may be disposed of or further recycled back to the reactor 203. The oil phase 212 may then enter a neutralization/waterwash apparatus 214 where substantially all the organic acids may be removed from the oil phase 212, resulting in at least a neutralized oil phase 215 and a waste stream 216. The neutralized oil phase 215 then may enter a dividing wall column 217, which may distill the neutralized oil phase 215.

The neutralized oil phase 215 may be similar to the neutralized oil phase 115 in FIG. 1. The dividing wall column 217 may be similar to the dividing wall column 117 in FIG. 1, with a condenser 218 and a reboiler 219.

The dividing wall column 217 may recover at least a top product 220, a middle product 221, and a bottom product 222. At least one nitroalkane may be recovered from the middle product 221. Examples of nitroalkanes that may be recovered include, among others, 2-nitropropane and nitrocyclohexane.

The bottom product 222 may include additional nitroalkanes. For example, the bottom product 222 may include 1-nitropropane, nitromethane, and nitroethane. The bottom product may enter a distillation column 223 to recover at least one additional nitroalkane. The distillation column 223 may distill the bottom product 222 such that at least a second top product 224 and a second bottom product 225 are produced. The second top product 224 may comprise an additional nitroalkane, for example, 1-nitropropane.

Figure 3:
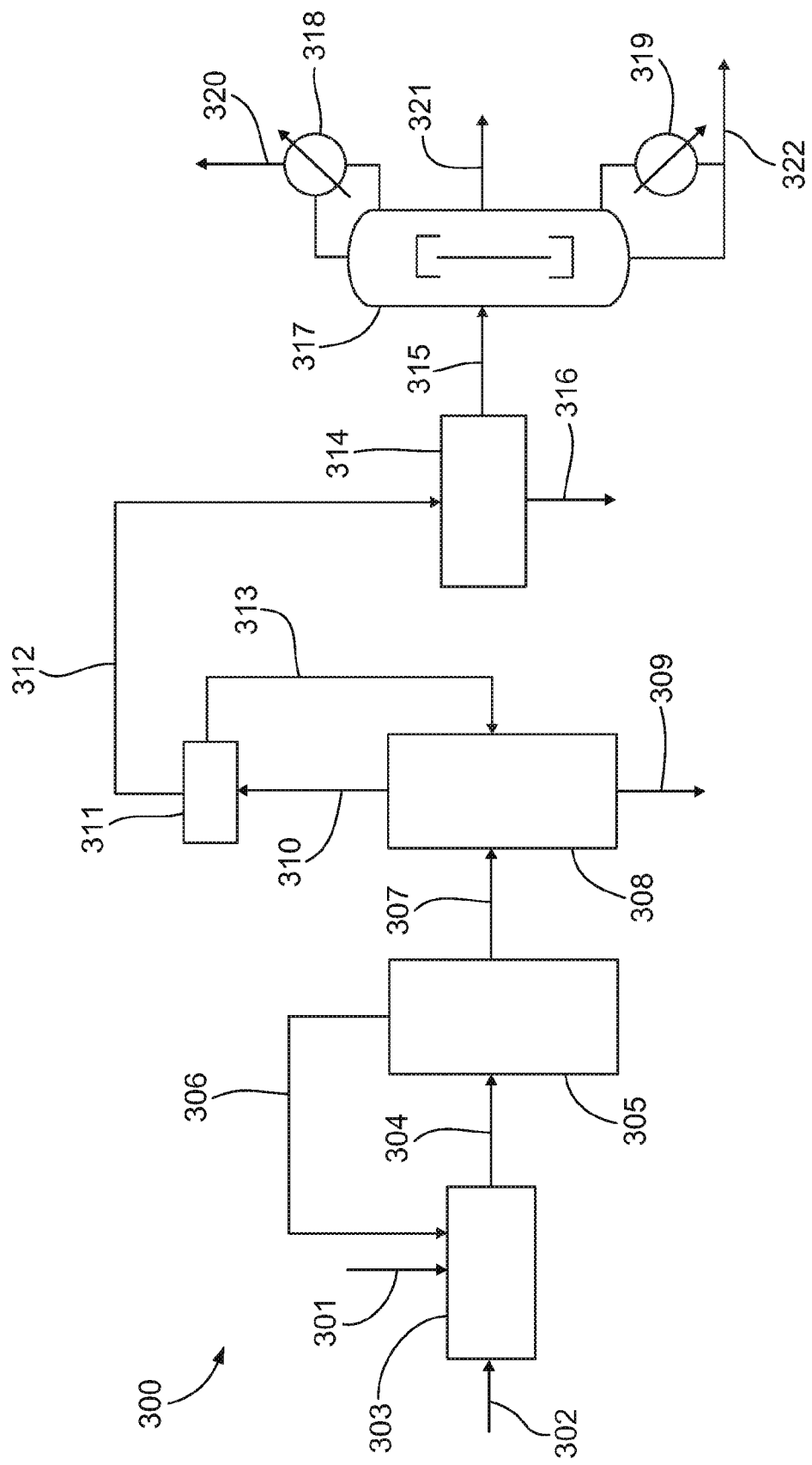
FIG. 3 is a schematic diagram of an apparatus for synthesizing at least one nitroalkane, in accordance with an illustrative embodiment.
Figure 4:
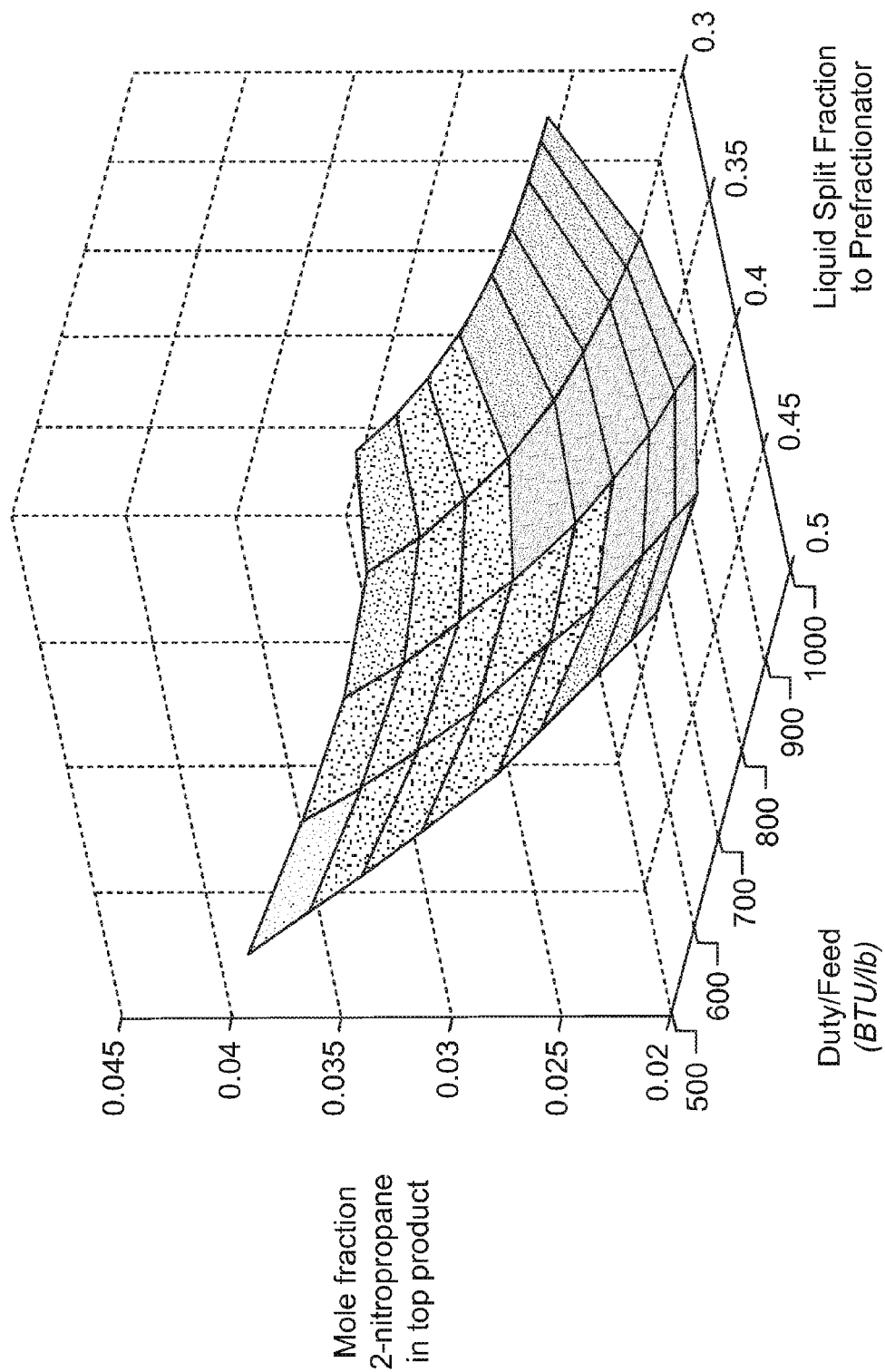
FIG. 4 is a graph of the mole fraction of 2-nitropropane in a top product as a function of liquid split ratio and duty for a high pressure nitration.
Figure 5:
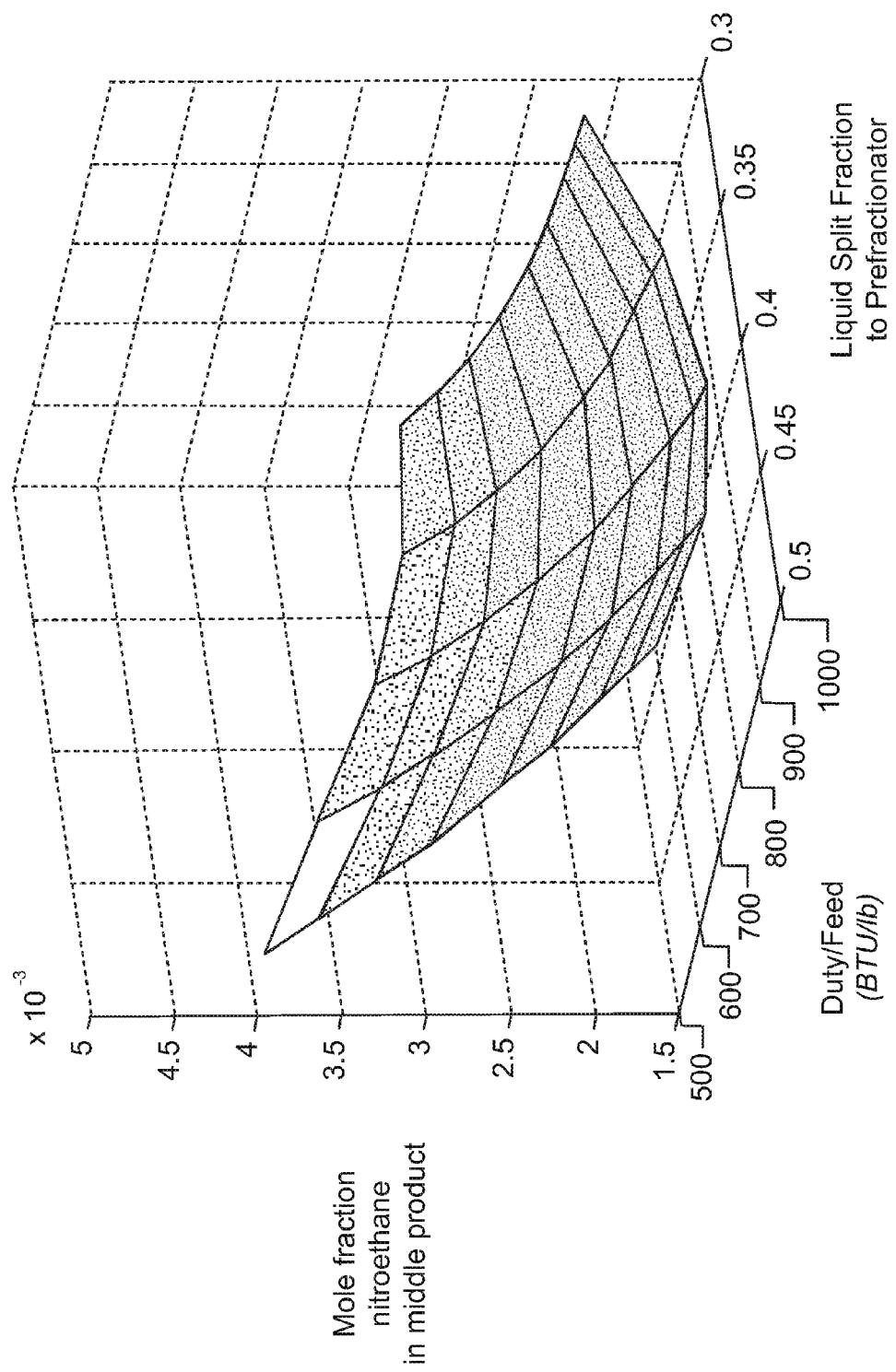
FIG. 5 is a graph of the mole fraction of nitroethane in a middle product as a function of liquid split ratio and duty for a high pressure nitration.
Figure 6:
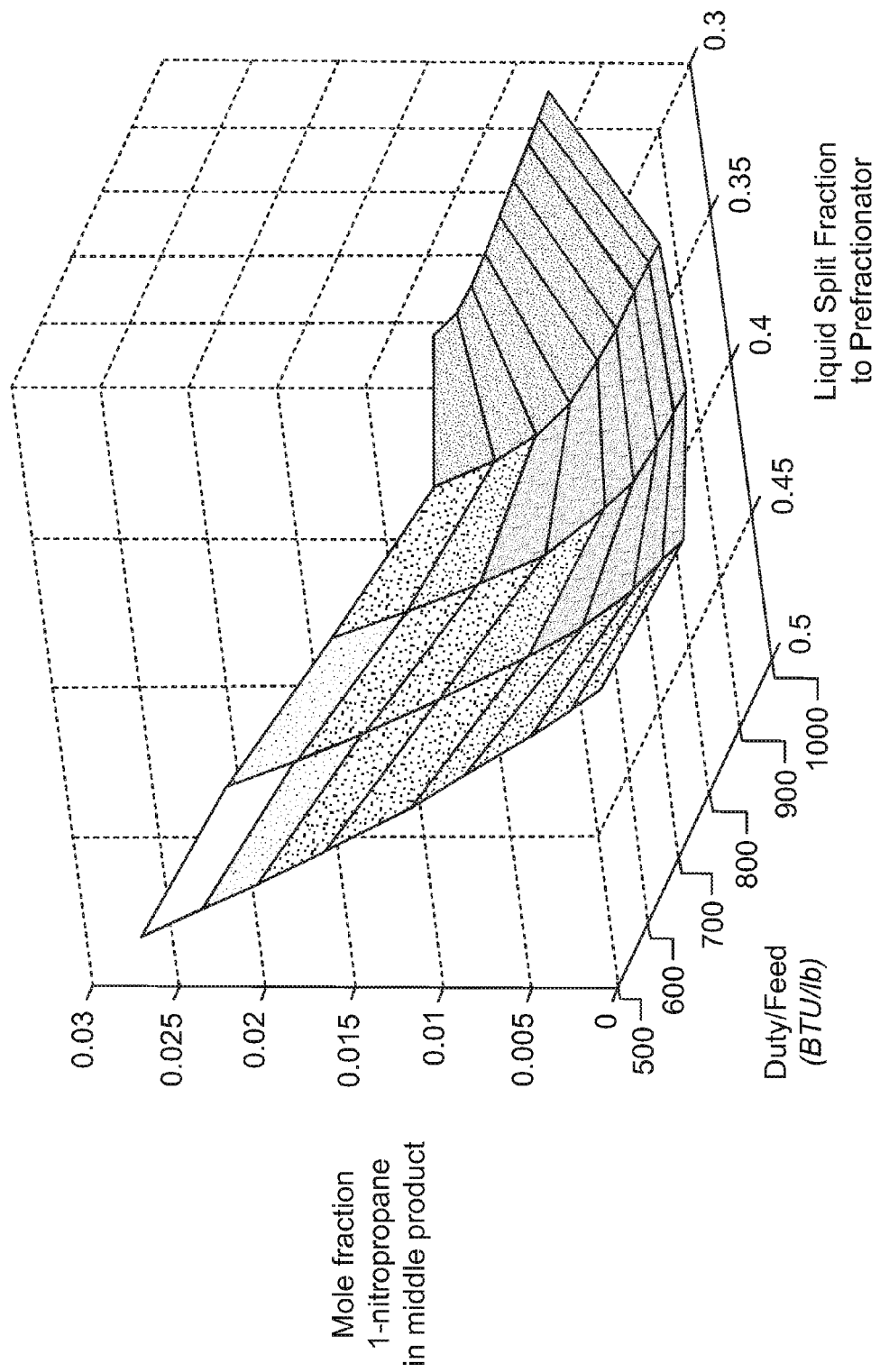
FIG. 6 is a graph of the mole fraction of 1-nitropropane in a middle product as a function of liquid split ratio and duty for a high pressure nitration.
Figure 7:
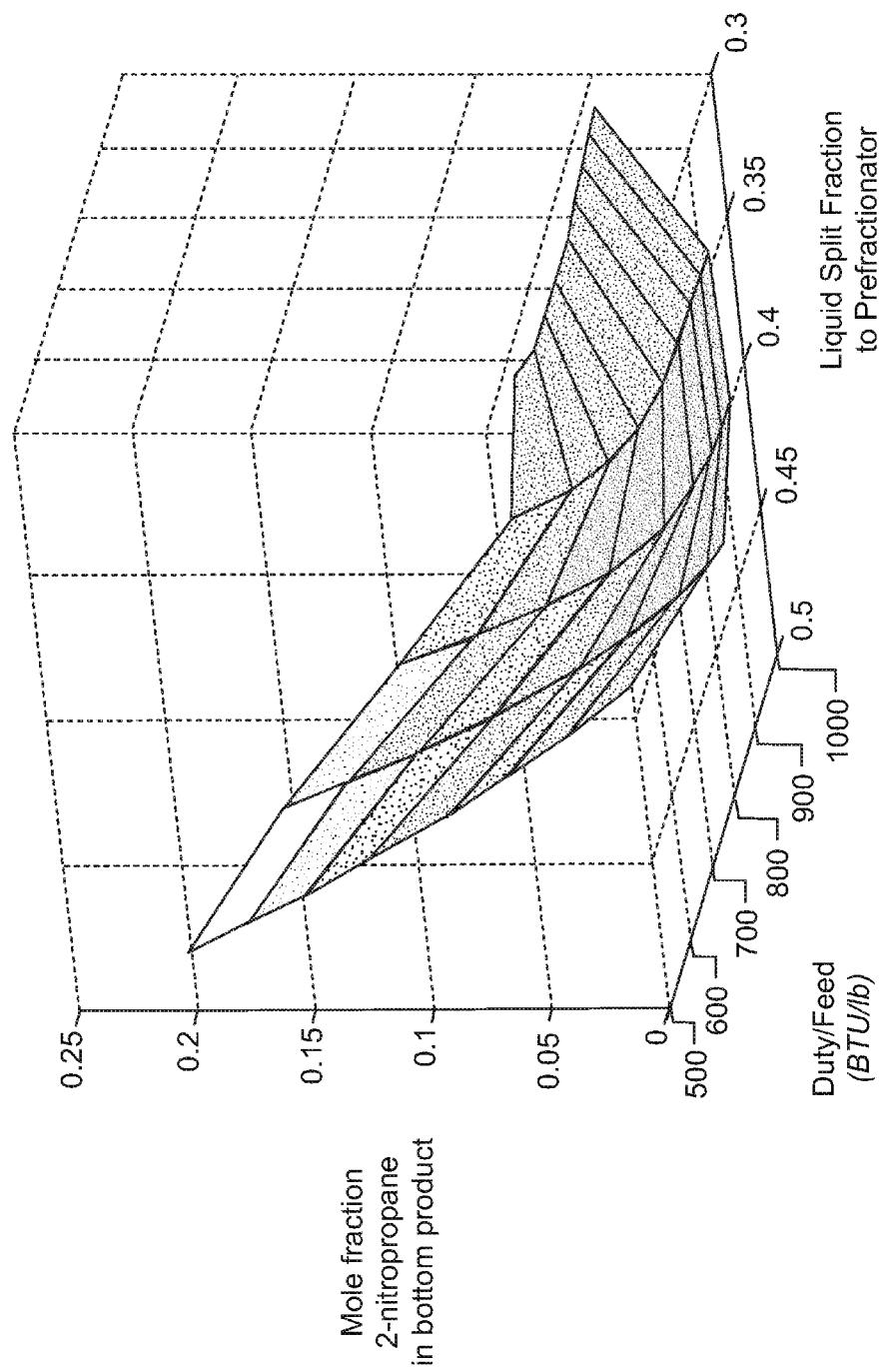
FIG. 7 is a graph of the mole fraction of 2-nitropropane in a bottom product as a function of liquid split ratio and duty for a high pressure nitration.

FIG. 3 illustrates an apparatus 300 for synthesizing at least one nitroalkane. A hydrocarbon feedstock 301 and aqueous nitric acid 302 may be introduced into a reactor 303. Reactor 303 may be similar to reactor 103 in FIG. 1. The hydrocarbon feedstock 301 and the aqueous nitric acid 302 may react at a reactor pressure and a reaction temperature, such that a product stream 304 comprising nitrated compounds and byproducts may be formed.

The hydrocarbon feedstock 301 and the aqueous nitric acid 302 may be mixed, or partially mixed, prior to entry into the reactor 303 or, alternatively; they may be added individually, with mixing to occur within the reactor 303. Further, hydrocarbon feedstock 301 and the aqueous nitric acid 302, whether added together or individually, may be preheated prior to entry into the reactor 303.

The hydrocarbon feedstock 301 may be similar to the hydrocarbon feedstock 101 in FIG. 1. The aqueous nitric acid 302 may have a similar composition as the aqueous nitric acid 102 in FIG. 1. The mole ratio of they hydrocarbon feedstock 301 to the aqueous nitric acid 302 may be at least about 0.3:1, more preferably at least about 0.5:1. The reactor pressure, reaction temperature, and residence time may be similar to that in FIG. 1.

The product stream 304 may then enter an absorber 305 for absorbing water-soluble and oil soluble components from the product stream 304 to form a hydrocarbon gas stream 306 and a gas-recovered mixture 307. The hydrocarbon gas stream 306 may contain unreacted hydrocarbons, carbon monoxide, carbon dioxide, nitric oxide, nitrous oxide, and nitrogen. The unreacted hydrocarbons in the hydrocarbon gas stream 306 may be recycled to the reactor 303. The remaining gases in the hydrocarbon gas stream 306 may be processed to recover nitric oxide as nitric acid. The further remaining gases in the hydrocarbon gas stream 306 may be sent through a burner and emitted. The gas-recovered mixture 307 may then enter a stripper 308 where an aqueous phase 309 may be stripped from the gas-recovered mixture 307 to form a second gas-recovered mixture 310. Next, the second gas-recovered mixture 310 may enter separator 311, where the second gas-recovered mixture 310 is separated into an oil phase 312 and a second aqueous phase 313. The second aqueous phase 313 may be recycled back to the phase separation apparatus 308. The aqueous phase 309 from the phase separation apparatus 308 may be disposed of or further recycled back to the reactor 303. For example, the aqueous phase 309 may contain organic acids, such as acetic acid, which may be returned to the reactor 303. The oil phase 312 may then enter a neutralization/water-wash apparatus 314 where substantially all the organic acids may be removed from the oil phase 312, resulting in at least a neutralized oil phase 315 and a waste stream 316. The neutralized oil phase 315 then may enter a dividing wall column 317, which may distill the neutralized oil phase 315.

The neutralized oil phase 315 may be similar to the neutralized oil phase 115 in FIG. 1. The dividing wall column 317 may be similar to the dividing wall column 117 in FIG. 1, with a condenser 318 and a reboiler 319.

The dividing wall column 317 may recover at least a top product 320, a middle product 321, and a bottom product 322. At least one nitroalkane may be recovered from the middle product 321. Examples of nitroalkanes that may be recovered include, among others, 2-nitropropane. In an illustrative embodiment, at least one nitroalkane is recovered from the top product 320. Examples of nitroalkanes that may be recovered include, among others, nitromethane.

In other illustrative embodiments, the neutralized oil phase 315 may enter a recovery apparatus for recovering a hydrocarbon prior to entering the dividing wall column 317. The recovery apparatus may recover, for example, cyclohexane, from the neutralized oil phase 315.

EXAMPLES

Various examples are demonstrated using a computer simulation.

Example 1

High Pressure Nitration of Propane

Propane is reacted with 30 weight percent aqueous nitric acid at a reactor pressure of about 1200 psi (77.4 atm), an average reaction temperature of about 250 degrees Celsius (a range of 220 to 290 degrees Celsius), a residence time of about 120 seconds, and a propane to nitric acid mole ratio of about 1.5:1 in a high pressure nitration process to produce a product stream. This product stream is then sent to a dividing wall column (DWC). The major components of the product stream feed to the DWC are summarized in Table 1 below. The scheme is designed for a 2-nitropropane production rate of 5420 lb/h. and consists of a relatively small fraction of components lighter than 2-nitropropane, followed by a large mole fraction of the desired product 2-nitropropane, and then a relatively small amount of components heavier than 2-nitropropane.

TABLE 1

| Feed to the DWC in a high pressure nitration process | |
|---|---|
| Temperature, ° C. | 21 |
| Pressure, atm | 1 |
| Mass flow, lb/h | 6071.8 |
| Mole fraction | |
| Water | 0.031554 |
| Nitrous oxide | 0.000254 |
| Propane | 0.020788 |
| Acetone | 0.027185 |
| Butane | 0.003291 |
| Nitromethane | 0.014159 |
| Nitroethane | 0.007774 |
| 2-nitropropane | 0.799292 |
| 1-nitropropane | 0.072607 |
| 1-nitrobutane | 5.56E−05 |
| 2-nitrobutane | 0.000223 |
| 2,2-dinitropropane | 0.022654 |
| Kerosene | 0.000158 |

The DWC is operated to separate the product stream into a top product, a middle product, and a bottom product. The top product from the DWC is essentially the volatiles (nitromethane, nitroethane, and acetone) along with water, the middle product is essentially pure 2-nitropropane, and the bottom product is essentially 1-nitropropane and heavies (nitrobutane, 2,2-dinitropropane, and kerosene). The DWC can be followed by another column to recover 1-nitropropane from the bottom product.

The desired purity of 2-nitropropane stream is 99.6% with a >99.5% recovery. The DWC design to achieve these specifications is shown below in Table 2. A total of 84 stages are required, with the feed stage at the $51^{st}$ stage from the condenser. The 2-nitropropane product draw-off is taken off from the $43^{rd}$ stage from the condenser.

Figure 8:
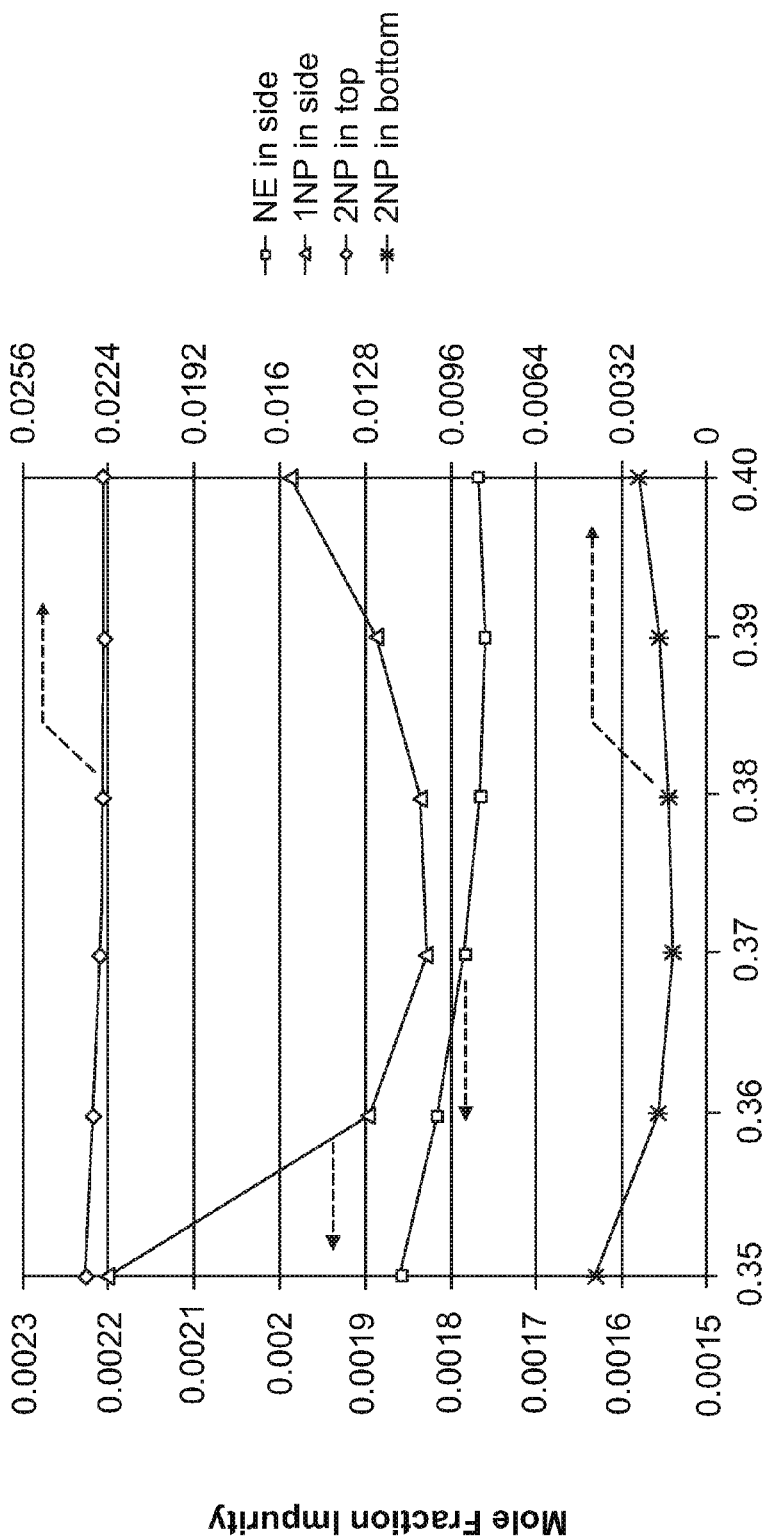
FIG. 8 is a graph of the impurity mole fraction as a function of liquid split ratio at an energy ratio of 881 BTU/lb for a high pressure nitration.
Figure 9:
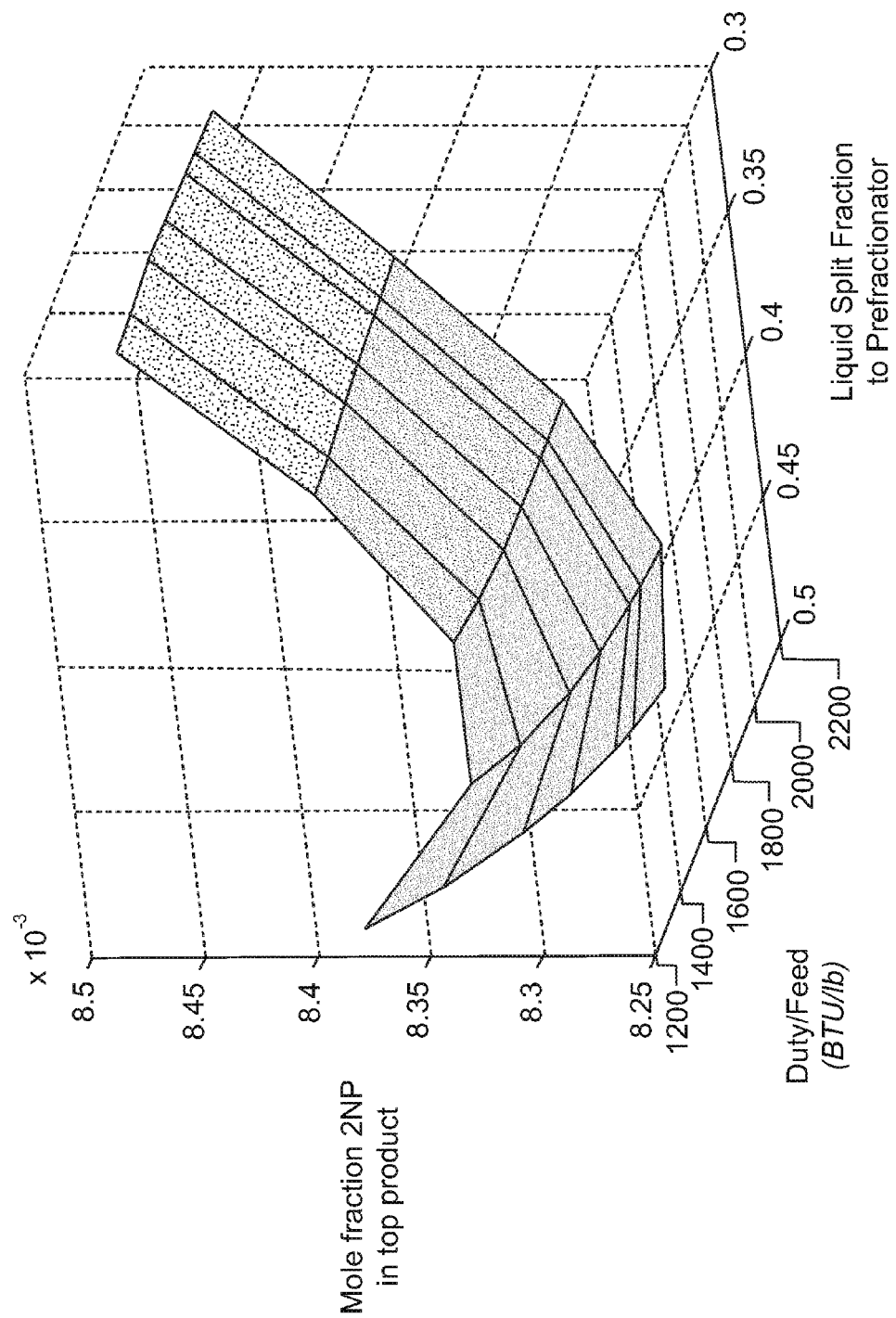
FIG. 9 is a graph of the mole fraction of 2-nitropropane in a top product as a function of liquid split ratio and duty for a vapor phase nitration.
Figure 10:
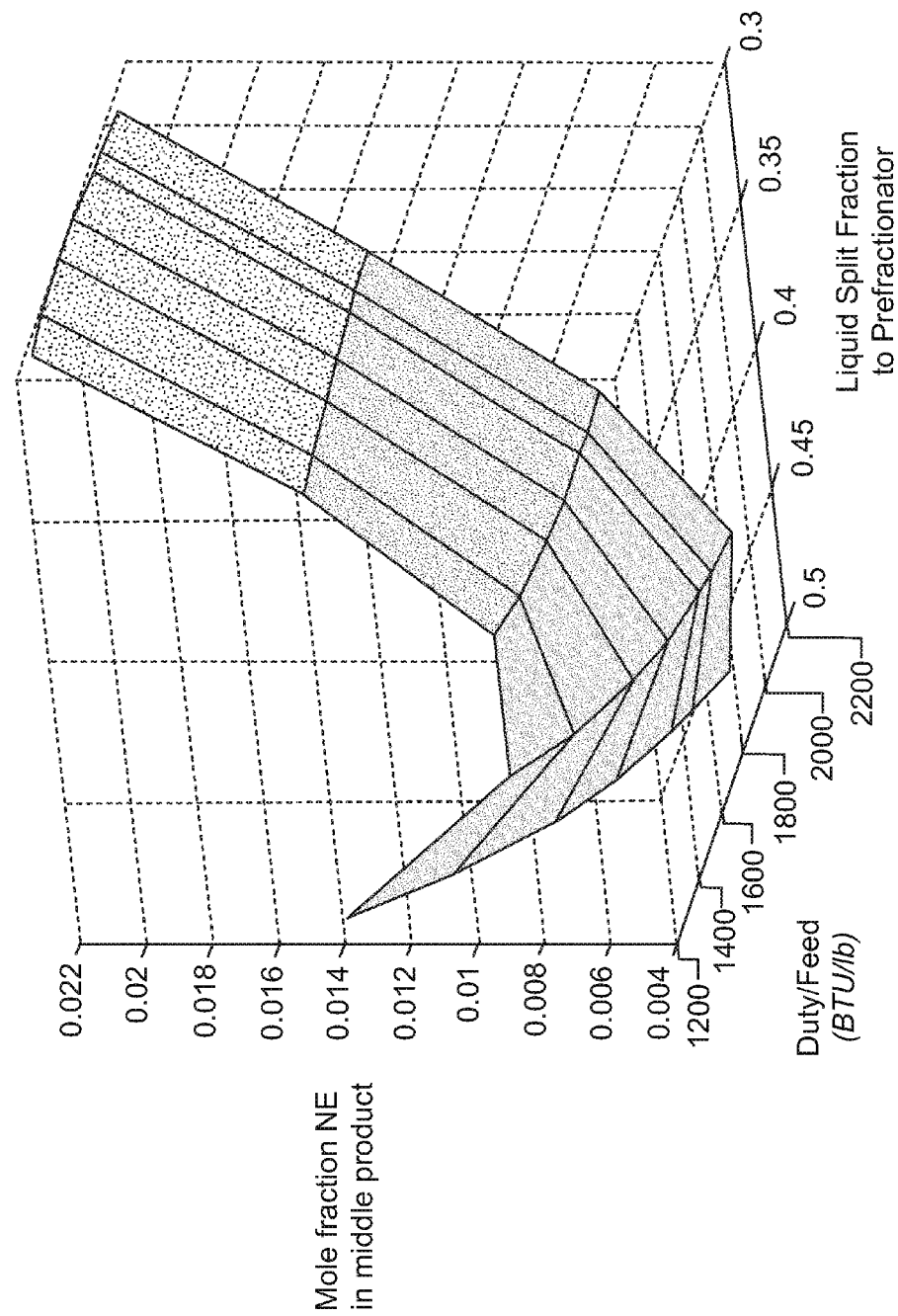
FIG. 10 is a graph of the mole fraction of nitroethane in a middle product as a function of liquid split ratio and duty for a vapor phase nitration.
Figure 11:
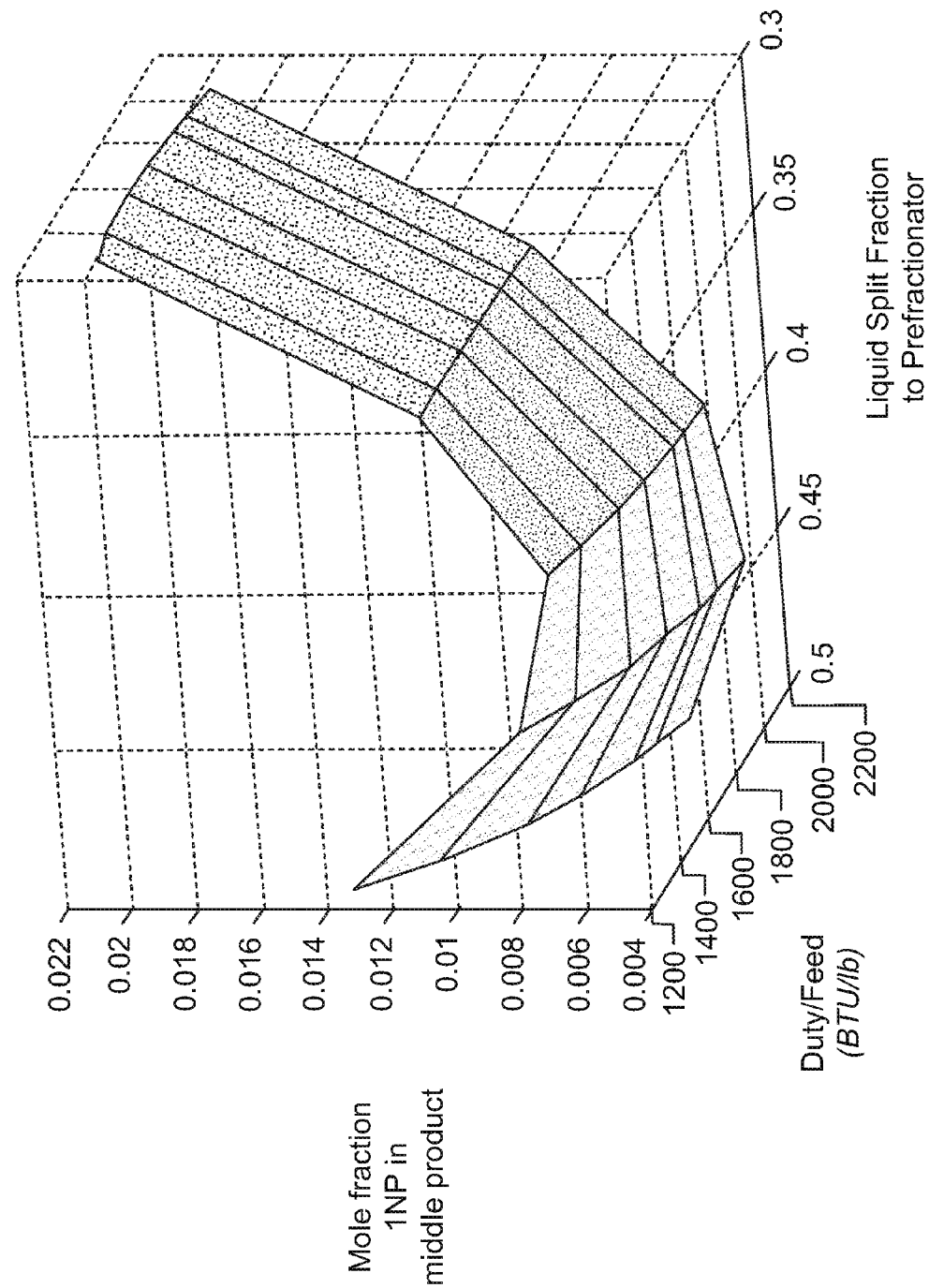
FIG. 11 is a graph of the mole fraction of 1-nitropropane in a middle product as a function of liquid split ratio and duty for a vapor phase nitration.
Figure 12:
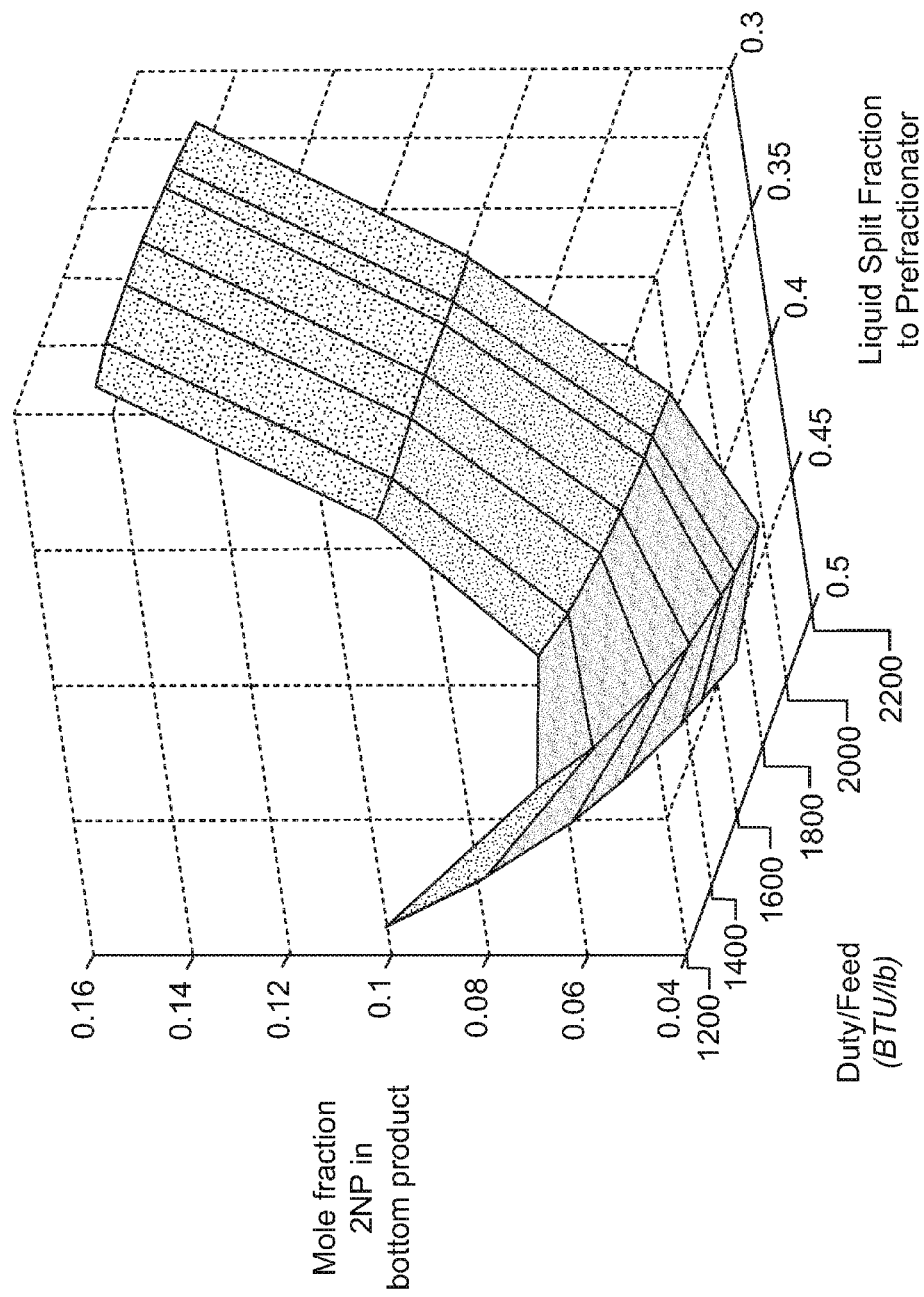
FIG. 12 is a graph of the mole fraction of 2-nitropropane in a bottom product as a function of liquid split ratio and duty for a vapor phase nitration.

The impurities include: 2-nitropropane in the top product, nitroethane and 1-nitropropane in the middle product, and 2-nitropropane in the bottom product. The impurity levels decrease as the reboiler duty is increased, as shown in FIGS. 4-7. FIGS. 4-7 illustrate the variation of the above impurities with respect to the percentage of liquid split that is sent to the pre-fractionator and the ratio of heat duty to feed, on a unit ratio basis (BTU/lb). The vapor split ratio is fixed to 50:50 whereas the optimum liquid split ratio with respect to reboiler duty is 37:63, as shown in FIG. 8. FIG. 8 illustrates a magnified section for the variation of impurity with liquid split ratio (0.35 to 0.40) at the energy unit ratio of 881 BTU/lb (a reboiler duty of 5.35 MMBTU/h). The minimum amount of 1-nitropropane impurity in the middle product and the 2-nitropropane impurity in the bottom product is at 37 percent of liquid feed to the pre-fractionator, therefore the optimum liquid split ratio for this example is 0.37:0.63.

Table 2 compares the simulation results using the product stream summarized in Table 1 above for a DWC set-up as compared to using the product stream in Table 1 for conventional scheme, using two distillation columns in the finishing train. The conventional sequence consumes 7.32 MM BTU/ hour for the separation requirements, using a total of 106 stages within the two distillation columns. The energy savings of the DWC are thus approximately 29% over the direct sequence. The single DWC that replaces both columns in the direct sequence is larger in diameter and area than either of the two columns it replaces, but only slightly so. A single DWC of 2.4 meters (8.15 feet) diameter replaces both the direct sequence columns.

TABLE 2

Comparison of DWC in high pressure nitration with direct sequence

|  | Divided Wall Column | Direct Scheme | |
| --- | --- | --- | --- |
|  |  | Column 1 | Column 2 |
| Eqm. No. of stages | 84 | 50 | 56 |
| Pressure, atm | 0.165 | 0.165 | 0.165 |
| Top temperature, °C. | 28.87 | 29.03 | 67 |
| Bottom temperature, °C. | 81.41 | 68.22 | 81.6 |
| Feed stage (from top) | 51 | 33 | 32 |
| Product stage | 43 | — | — |
| Liquid split ratio | 0.37:0.63 |  |  |
| Vapor split ratio | 0.5:0.5 |  |  |
| Reboiler duty, MMBTU/h | 5.35 | 3.77 | 3.71 |
| Condenser duty, MMBTU/h | −5.04 | −3.47 | −3.7 |
| Column diameter, m | 1.75 | 1.47 | 1.45 |
| Volatiles, lbmol/h | 7.53 | 7.53 |  |
| Water (mole fraction) | 0.29770264 | 0.297668 |  |
| Nitrous oxide | 0.00240066 | 0.0024 |  |
| Propane | 0.19619249 | 0.196169 |  |
| Acetone | 0.25649699 | 0.256467 |  |
| Butane | 0.03104843 | 0.031045 |  |
| Nitromethane | 0.1335381 | 0.133563 |  |
| Nitroethane | 0.05980164 | 0.060056 |  |
| 2-nitropropane | 0.0227673 | 0.02258 |  |
| 2-nitropropane stream, lbmol/h | 56.794 |  | 56.794 |
| Nitroethane (mole fraction) | 0.00179863 |  | 0.001761 |
| 2-nitropropane | 0.99635095 |  | 0.996478 |
| 1-nitropropane | 0.00184499 |  | 0.001761 |
| 1-nitropropane stream, lbmol/h | 7.19 |  | 7.19 |
| 2-nitropropane (mole fraction) | 0.0014739 |  | 0.000683 |
| 1-nitropropane | 0.70303699 |  | 0.703813 |
| 1-nitrobutane | 0.00054958 |  | 0.00055 |
| 2-nitrobutane | 0.0022033 |  | 0.002203 |
| 2,2-dinitropropane | 0.29117152 |  | 0.291186 |
| Kerosene | 0.00156467 |  | 0.001565 |

Example 2

Vapor Phase Nitration of Propane

Vapor phase nitration has a lower selectivity towards 2-nitropropane. Propane is reacted with 70 weight percent aqueous nitric acid at a reactor pressure of about 185 psi (9.7 atm), an average reaction temperature of about 370 degrees Celsius, a residence time of about 2.3 seconds, and a propane to nitric acid mole ratio of about 4:1 in a vapor phase nitration process to produce an product stream. Table 3 summarizes a typical composition of the product stream coming out of the water-wash neutralization section from a vapor phase nitration process compared with the stream composition of a similar stream from a high pressure nitration process.

TABLE 3

Composition of key components in input to the downstream purification section of vapor phase nitration and high pressure nitration process

|  | Weight % | |
| --- | --- | --- |
| Components | Vapor | High Pressure |
| Nitromethane | 20.4 | 1.01 |
| Nitroethane | 5.0 | 0.6 |
| 2-nitropropane | 56.5 | 83.3 |
| 1-nitropropane | 15.7 | 7.6 |

This product stream is then sent to a dividing wall column (DWC). The major components of the product stream feed to the DWC are summarized in Table 4 below.

TABLE 4

Feed to the DWC in a vapor phase nitration process

| Temperature, °C. | 21 |
| --- | --- |
| Pressure, atm | 1 |
| Mass flow, lb/h | 2343.87 |
| Mole fraction |  |
| Water | 0.0853 |
| Nitromethane | 0.2513 |
| Nitroethane | 0.0502 |
| 2-nitropropane | 0.4779 |
| 1-nitropropane | 0.1323 |
| 2-nitrobutane | 0.0029 |

In vapor phase nitration, more of the lower nitroalkanes (nitromethane, nitroethane, and 1-nitropropane) are formed as compared to high pressure nitration and therefore the weight fraction of 2-nitropropane is significantly less. The energy and capital benefits as a result of a DWC are directly proportional to the weight fraction of the middle component in the feed stream, which in this case is 2-nitropropane.

Figure 13:
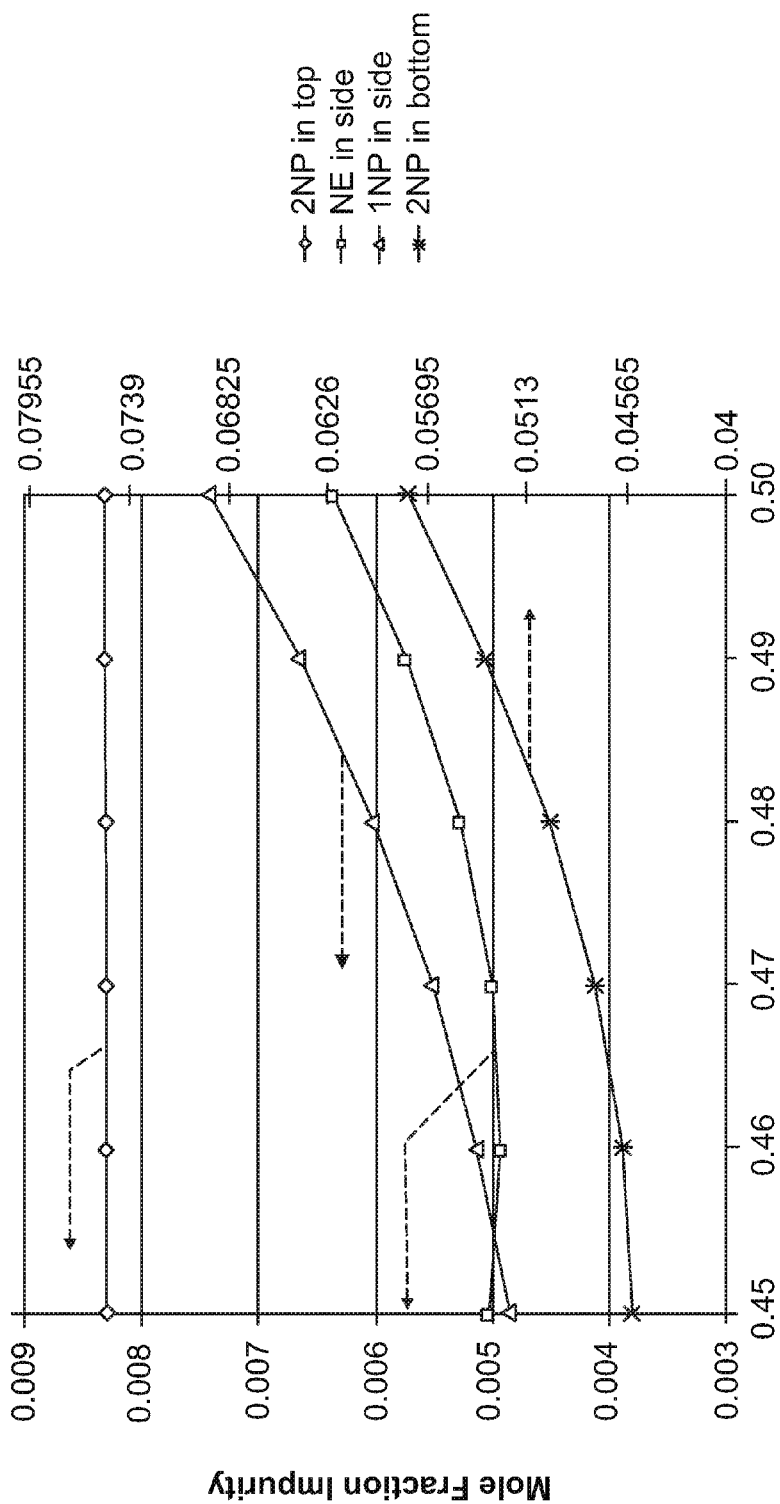
FIG. 13 is a graph of the impurity mole fraction as a function of liquid split ratio at an energy ratio of 1855 BTU/lb for a vapor phase nitration.
Figure 14:
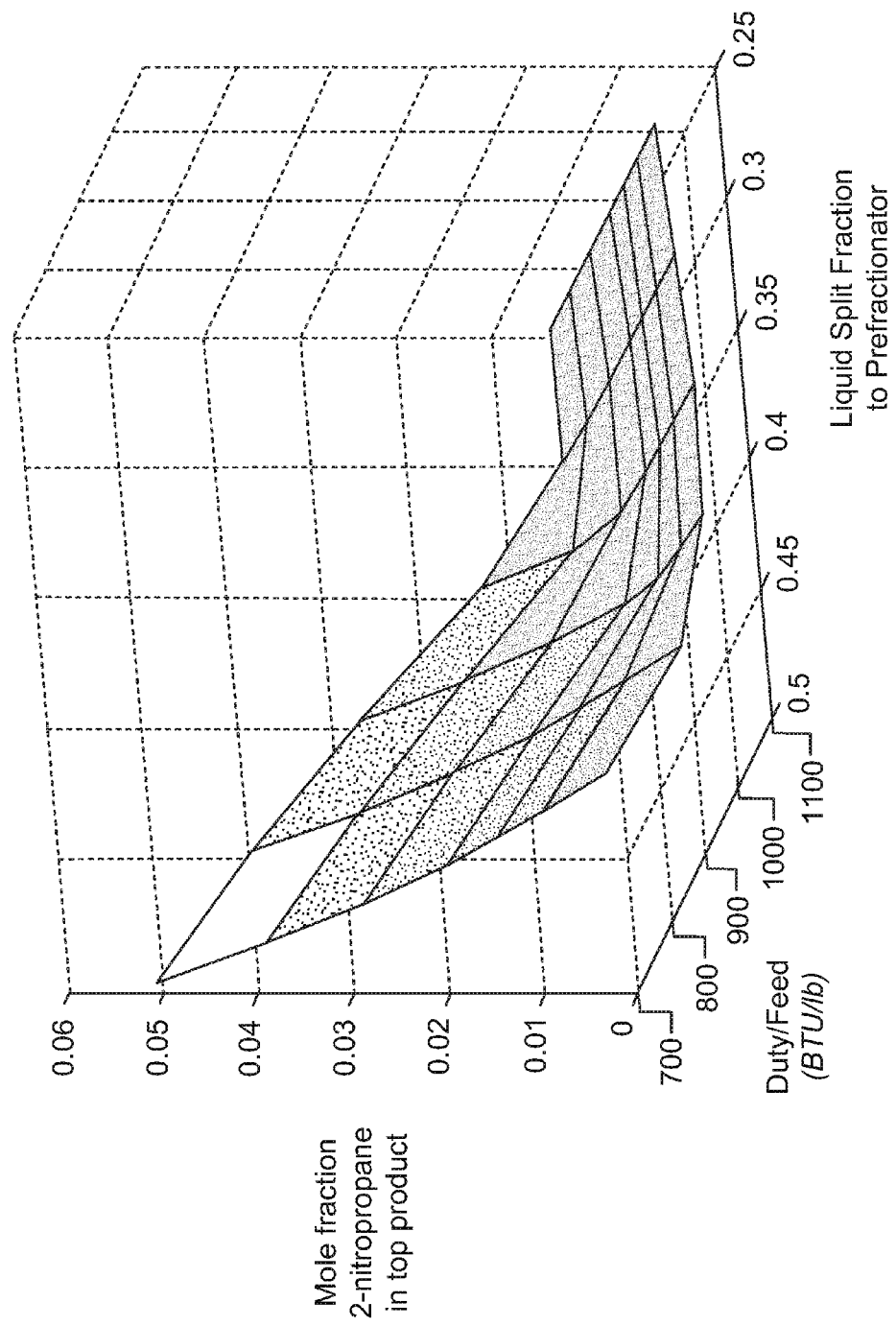
FIG. 14 is a graph of the mole fraction of 2-nitropropane in a top product as a function of liquid split ratio and duty for a modified high pressure nitration.
Figure 15:
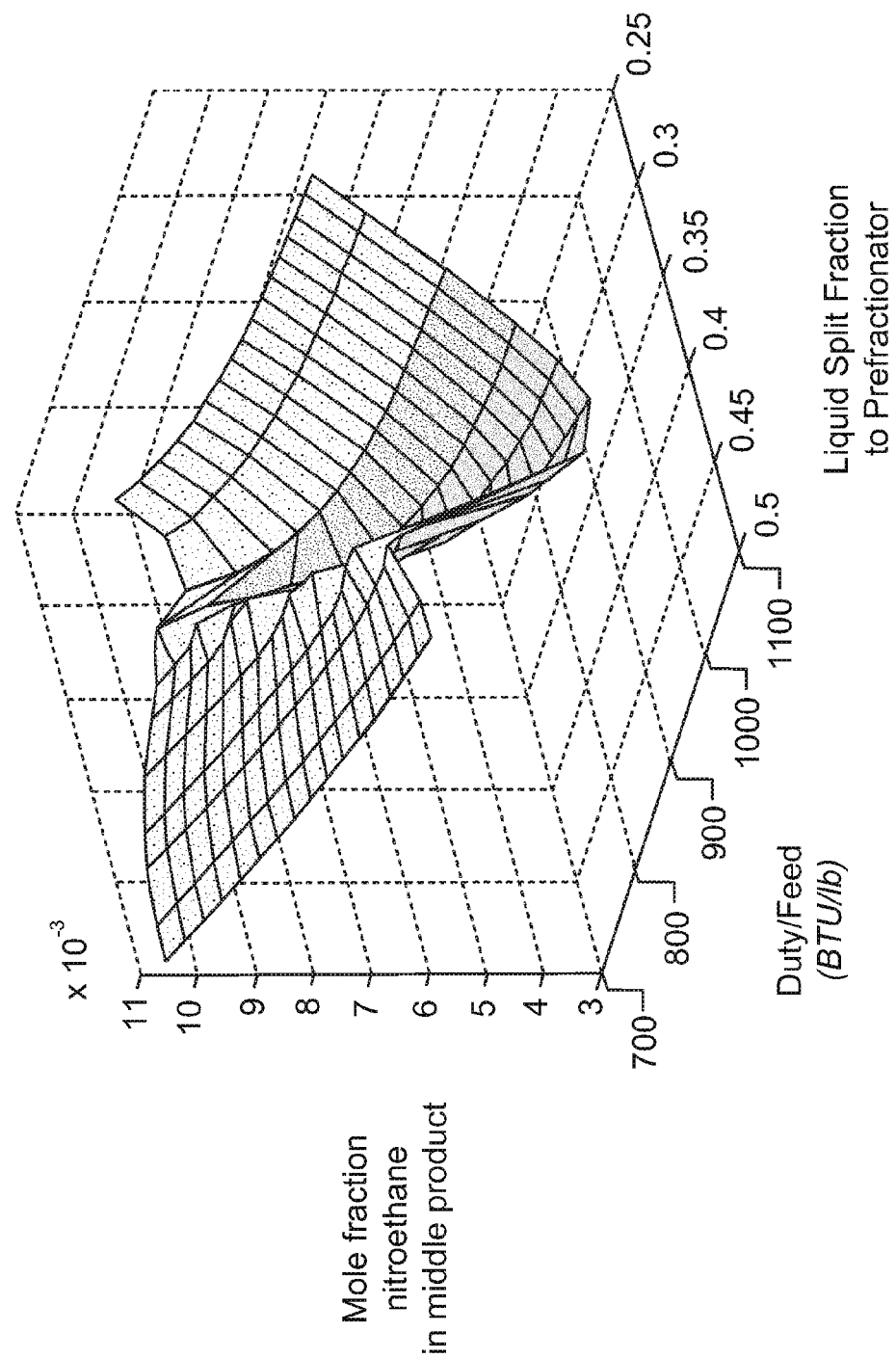
FIG. 15 is a graph of the mole fraction of nitroethane in a middle product as a function of liquid split ratio and duty for a modified high pressure nitration.
Figure 16:
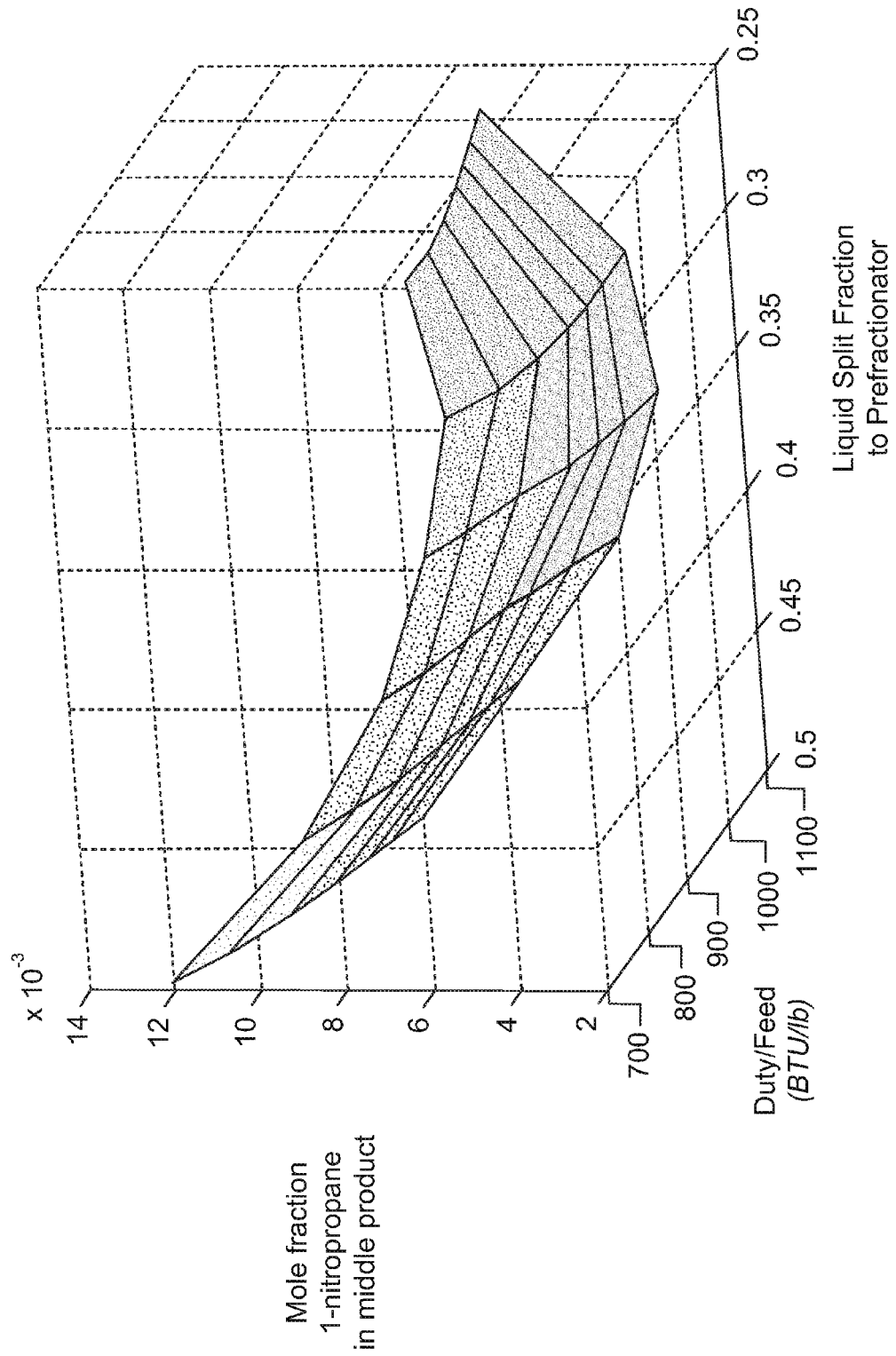
FIG. 16 is a graph of the mole fraction of 1-nitropropane in a middle product as a function of liquid split ratio and duty for a modified high pressure nitration.
Figure 17:
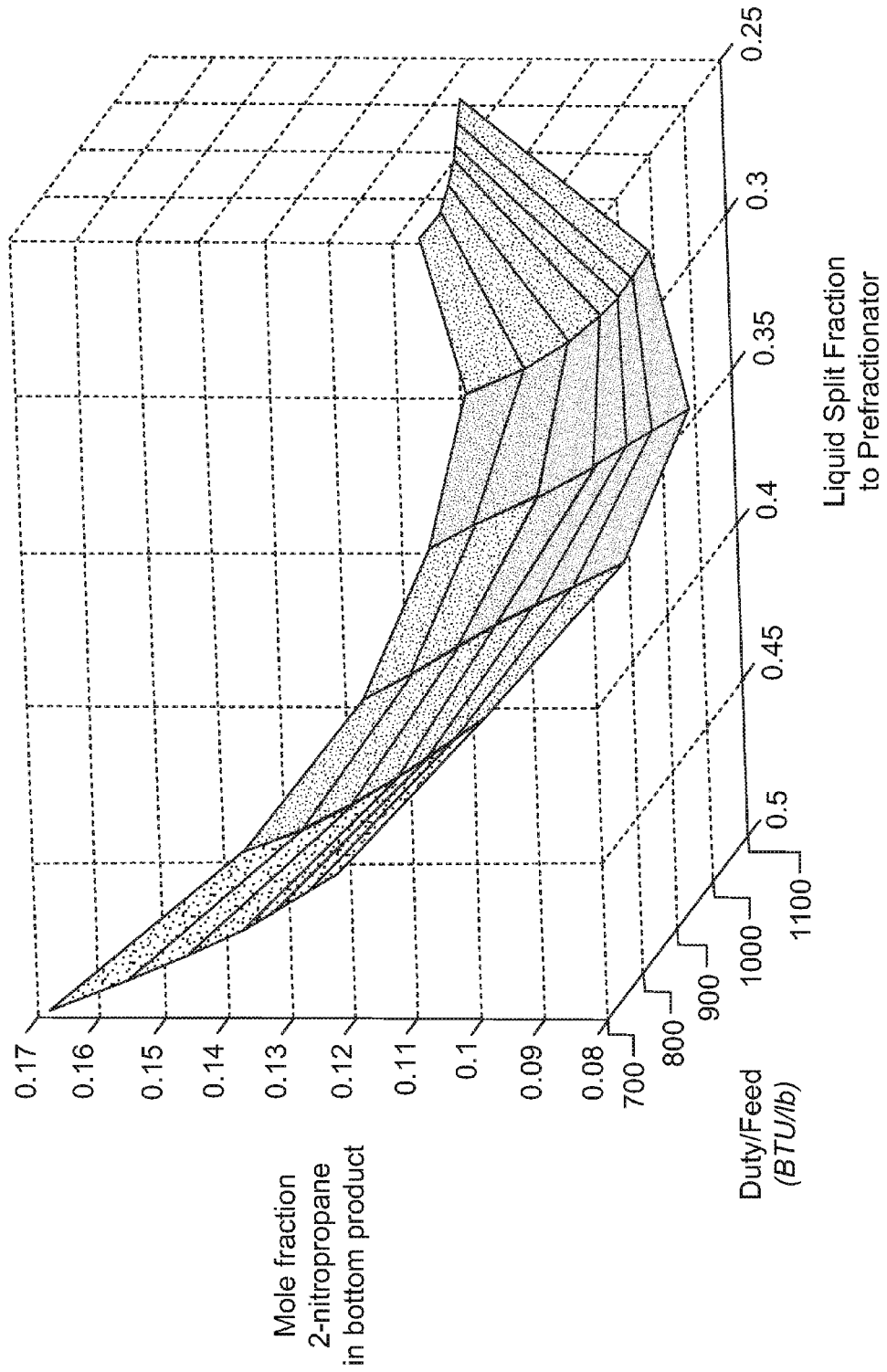
FIG. 17 is a graph of the mole fraction of 2-nitropropane in a bottom product as a function of liquid split ratio and duty for a modified high pressure nitration.

Similar to Example 1, the impurities include: 2-nitropropane in the top product, nitroethane and 1-nitropropane in the middle product, and 2-nitropropane in the bottom product. The impurity levels decrease as the reboiler duty is increased, as shown in FIGS. 9-12. FIGS. 9-12 illustrate the variation of the above impurities with respect to the percentage of liquid split that is sent to the pre-fractionator and the ratio of heat duty to feed, on a unit ratio basis (BTU/lb). The vapor split ratio is fixed to 50:50 whereas the optimum liquid split ratio with respect to reboiler duty is 46:54, as shown in FIG. 13. FIG. 13 illustrates a magnified section for the variation of impurity with liquid split ration (0.45 to 0.5) at the energy unit ratio of 1835 BTU/lb (a reboiler duty of 4.35 MMBTU/h). The minimum amount of 2-nitropropane impurity in the top product and nitroethane impurity in the middle product is at a 47 percent liquid feed to the pre-fractinator, but the amount of 1-nitropropane impurity in the middle product and the 2-nitropropane impurity in the bottom product rise steeply beyond 46 percent, therefore the optimum liquid split ratio for this example is 0.46:0.64.

A comparison of a proposed DWC separation using the product stream summarized in Table 4 above with a conventional direct scheme using the product stream in Table 4 is shown in Table 5 below.

TABLE 5

Comparison of DWC scheme with Direct Scheme for vapor phase nitration

| | Divided Wall Column | Direct Sequence Column 1 | Direct Sequence Column 2 |
|---|---|---|---|
| Eqm. No. of stages | 72 | 46 | 41 |
| Pressure, atm | 0.165 | 0.165 | 0.165 |
| Top temperature, ° C. | 41.7 | 47.5 | 66.9 |
| Bottom temperature,° C. | 77.6 | 68.9 | 77 |
| Feed stage (from top) | 45 | 31 | 24 |
| Product stage | 41 | — | — |
| Liquid split ratio | 0.46:0.54 | — | — |
| Vapor split ratio | 0.5:0.5 | — | — |
| Reboiler duty, MMBTU/h | 4.35 | 4.71 | 1.1 |
| Condenser duty, MMBTU/h | −4.1 | −4.45 | −1.1 |
| Column diameter, m | 2.1 | 1.64 | 0.78 |
| Volatiles, lbmol/h | 12.0638 | 12.0643 | — |
| Water (mole fraction) | 0.2199 | 0.2199 | — |
| Nitromethane | 0.6483 | 0.6483 | — |
| Nitroethane | 0.1234 | 0.1235 | — |
| 2-nitropropane | 0.0083 | 0.0083 | — |
| 2-nitropropane stream, lbmol/h | 14.7217 | — | 14.7217 |
| Nitromethane (mole fraction) | 1.3E−06 | — | 8.5E−08 |
| Nitroethane | 0.0049 | — | 0.0049 |
| 2-nitropropane | 0.9899 | — | 0.9903 |
| 1-nitropropane | 0.0051 | — | 0.0048 |
| 1-nitropropane stream, lbmol/h | 4.3334 | — | 4.3328 |
| Nitroethane (mole fraction) | 3.4E−06 | — | 4.8E−06 |
| 2-nitropropane | 0.0459 | — | 0.0447 |
| 1-nitropropane | 0.9330 | — | 0.9342 |
| 2-nitrobutane | 0.0211 | — | 0.0211 |

According to the direct scheme, a 99.05% pure 2-nitropropane product specification requires two columns with 87 total equilibrium stages, whereas a single dividing wall column with 72 equilibrium stages achieves the same specifications utilizing 25% less energy. The feed to the DWC enters at the $45^{th}$ stage from the condenser and the 2-nitropropane product draw-off is taken off from the $41^{st}$ stage from the condenser.

Example 3

Modified High Pressure Nitration

In a modified version of the high pressure process, the main oxidation byproducts (carboxylic acids) are recycled to produce valuable nitroparaffin products rather than discarded to wastewater treatment. Propane is reacted with 30 weight percent nitric acid at a reactor pressure of about 1200 psi (77.4 atm), an average reaction temperature of about 235 degrees Celsius (a range of 180 to 290 degrees Celsius), a residence time of about 120 seconds, and a propane to nitric acid mole ratio of about 0.5:1. The main byproduct of propane nitration is acetic acid in high pressure nitration (acetic acid may also be added at startup in order to more quickly obtain a steady-state process). This byproduct, when concentrated and recycled to the reactor yields significant amounts of nitromethane at typical high pressure nitration process conditions. Nitromethane selectivity is about 55%, which is about 30% higher than the maximum achievable using the commercial technology. The composition of a typical product stream coming out of the water-wash neutralization section of the modified high pressure process is summarized in Table 6 below and is compared with the high pressure and vapor phase (commercial process) streams.

TABLE 6

Composition of key components in input to the downstream purification section of vapor phase nitration, high pressure nitration and modified high pressure nitration process

| | weight % | | |
|---|---|---|---|
| Components | High Pressure | Vapor | Modified High Pressure |
| Nitromethane | 1.01 | 20.4 | 55 |
| Nitroethane | 0.6 | 5.0 | 1 |
| 2-nitropropane | 83.3 | 56.5 | 40 |
| 1-nitropropane | 7.6 | 15.7 | 4 |

The composition of the middle boiling component 2-nitropropane progressively decreases from high pressure to modified high pressure process; therefore the benefits due to using a DWC would also follow the same trend. Nevertheless, the capital and energy savings still exist, as is shown in the analysis below. The product stream is then sent to a dividing wall column (DWC). The major components of the product stream feed to the DWC are summarized in Table 7 below.

TABLE 7

Feed to the DWC in a modified high pressure process

| | |
|---|---|
| Temperature, ° C. | 21 |
| Pressure, atm | 1 |
| Mass flow, lb/h | 5200 |
| Mole fraction | |
| Nitromethane | 0.6398 |
| Nitroethane | 0.0095 |
| 2-Nitropropane | 0.3188 |
| 1-Nitropropane | 0.0319 |

Figure 18:
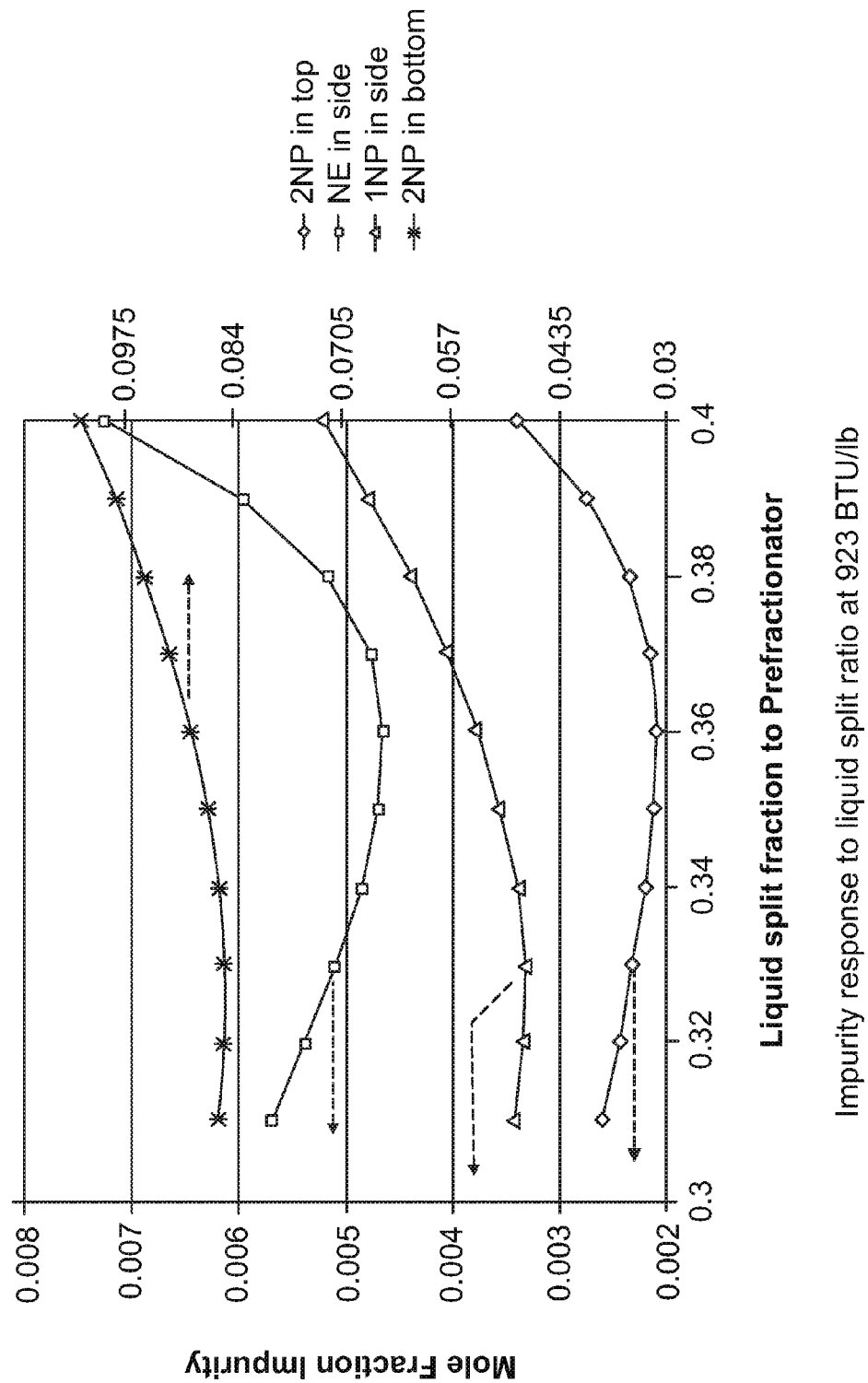
FIG. 18 is a graph of the impurity mole fraction as a function of liquid split ratio at an energy ratio of 923 BTU/lb for a modified high pressure nitration.

Similar to Examples 1 and 2, the impurities include: 2-nitropropane in the top product, nitroethane and 1-nitropropane in the middle product, and 2-nitropropane in the bottom product. The impurity levels decrease as the reboiler duty is increased, as shown in FIGS. 14-17. FIGS. 14-17 illustrate the variation of the above impurities with respect to the percentage of liquid split that is sent to the pre-fractionator and the ratio of heat duty to feed, on a unit ratio basis (BTU/lb). The vapor split ratio is fixed to 50:50 whereas the optimum liquid split ratio with respect to reboiler duty is 46:54, as shown in FIG. 18. FIG. 18 illustrates a magnified section for the variation of impurity with liquid split ration (0.3 to 0.4) at the energy unit ratio of 923 BTU/lb (a reboiler duty of 4.8 MMBTU/h). The minimum amount of 2-nitropropane impurity in the top product and nitroethane impurity in the middle product is at 36 percent liquid feed to the pre-fractionator, but the amount of 1-nitropropane impurity in the middle product and the 2-nitropropane impurity in the bottom product rise steeply beyond 35 percent, therefore the optimum liquid split ratio for this example is 0.35:0.65

A comparison of the proposed DWC set-up using the product stream summarized in Table 7 above with the conventional scheme using the product stream in Table 7 is shown in Table 8 below.

TABLE 8

DWC comparison with direct scheme for modified high pressure process

| | Divided Wall Column | Direct Scheme Column 1 | Direct Scheme Column 2 |
|---|---|---|---|
| Eqm. No. of stages | 76 | 55 | 35 |
| Pressure, atm | 0.165 | 0.165 | 0.165 |
| Top temperature, °C. | 51.5 | 51.5 | 67 |
| Bottom temperature, °C. | 76.14 | 67.7 | 76.11 |
| Feed stage (from top) | 46 | 42 | 20 |
| Product stage | 53 | — | — |
| Liquid split ratio | 0.35:0.65 | — | — |
| Vapor split ratio | 0.5:0.5 | — | — |
| Reboiler duty, MMBTU/h | 4.8 | 4.7 | 1.5 |
| Condenser duty, MMBTU/h | −3.9 | −3.8 | −1.5 |
| Column diameter, m | 2.3 | 1.65 | 0.92 |
| Volatiles, lbmol/h | 47.5382 | 47.54685 | — |
| Nitromethane (mole fraction) | 0.9856 | 0.9854 | — |
| Nitroethane | 0.0123 | 0.0125 | — |
| 2-nitropropane | 0.0021 | 0.0021 | — |
| 2-nitropropane stream, lbmol/h | 23.2226 | — | 23.2226 |
| Nitromethane (mole fraction) | 2.8E−06 | — | 4.8E−06 |
| Nitroethane | 0.0047 | — | 0.0043 |
| 2-nitropropane | 0.9918 | — | 0.9910 |
| 1-nitropropane | 0.0036 | — | 0.0047 |
| 1-nitropropane stream, lbmol/h | 2.4668 | — | 2.4582 |
| Nitroethane (mole fraction) | 5.3E−06 | — | 8.4E−06 |
| 2-nitropropane | 0.0871 | — | 0.0946 |

According to the direct scheme, a 99.18% pure 2-nitropropane product specification would require two columns consisting of a total of 90 equilibrium stages, whereas a single dividing wall column with 76 equilibrium stages achieves the same specifications utilizing about 22% less energy. The feed to the DWC enters at the 46$^{th}$ stage from the condenser and the 2-nitropropane product draw-off is taken off from the 53$^{rd}$ stage from the condenser. A reboiler duty of 4.8 MMBTU/h is required to process a feed stream of 5200 lb/h.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for synthesizing at least one nitroalkane, the process comprising:
reacting in a reactor a hydrocarbon feedstock with aqueous nitric acid, such that a product stream is produced;
separating the product stream into at least an oil phase and an aqueous phase;
removing substantially all organic acids from the oil phase;
thereafter, distilling the oil phase in a dividing wall column, to recover at least a top product, a middle product, and a bottom product; and
recovering the at least one nitroalkane from the middle product.

2. A process according to claim 1, further comprising returning the organic acids to the reactor.

3. A process according to claim 2, further comprising recovering nitromethane from the top product, wherein the organic acids comprise acetic acid.

4. A process according to claim 1, wherein the dividing wall column comprises a condenser and a reboiler.

5. A process according to claim 4, wherein the condenser is operated at a temperature between 20 and 80 degrees Celsius.

6. A process according to claim 4, wherein the reboiler is operated at a temperature between 75 and 85 degrees Celsius.

7. A process according to claim 1, wherein the dividing wall column is operated at a vapor split ratio of about 0.5:0.5.

8. A process according to claim 1, wherein the dividing wall column is operated at a liquid split ratio of about 0.37:0.63.

9. A process according to claim 1, wherein the dividing wall column is operated at a liquid split ratio of about 0.46:0.54.

10. A process according to claim 1, wherein the dividing wall column is operated at a liquid split ratio of about 0.35:0.65.

11. A process according to claim 1, wherein the at least one nitroalkane is 2-nitropropane.

12. A process according to claim 11, further comprising:
distilling the bottom product to recover at least one additional nitroalkane.

13. A process according to claim 12, wherein the at least one additional nitroalkane is 1-nitropropane.

14. A process for nitroalkane recovery, the process comprising:
separating a product stream from a nitroparaffin nitration process into at least an oil phase and an aqueous phase;
distilling the oil phase in a dividing wall column, to recover at least a top product, a middle product, and a bottom product;
recovering at least a first nitroalkane from the middle product; and
recovering at least a second nitroalkane from the bottom product.

15. A process according to claim 14, wherein the first nitroalkane is 2-nitropropane.

16. A process according to claim 15, wherein the second nitroalkane is 1-nitropropane.

* * * * *